(12) United States Patent
Shan et al.

(10) Patent No.: US 8,642,094 B2
(45) Date of Patent: Feb. 4, 2014

(54) SYNERGISTIC PHARMACEUTICAL COMPOSITION, METHOD OF MAKING SAME AND USE OF SAME

(75) Inventors: Jacqueline J. Shan, Edmonton (CA); Lei Ling, Edmonton (CA); Vinti Goel, Edmonton (CA); Guizhong Qi, Edmonton (CA); Shaozhao Wang, Edmonton (CA)

(73) Assignee: Afexa Life Sciences Inc. (CA)

( * ) Notice: Subject to any disclaimer, the term of this patent is extended or adjusted under 35 U.S.C. 154(b) by 683 days.

(21) Appl. No.: 12/434,289

(22) Filed: May 1, 2009

(65) Prior Publication Data

US 2009/0285915 A1 Nov. 19, 2009

Related U.S. Application Data

(60) Provisional application No. 61/049,588, filed on May 1, 2008.

(51) Int. Cl.
*A61K 36/00* (2006.01)
*A61K 36/73* (2006.01)

(52) U.S. Cl.
USPC .......................................... 424/725; 424/765

(58) Field of Classification Search
None
See application file for complete search history.

(56) References Cited

U.S. PATENT DOCUMENTS

2005/0025843 A1* 2/2005 Shen et al. .................... 424/728
2010/0239603 A1* 9/2010 Wang et al. .............. 424/195.16

FOREIGN PATENT DOCUMENTS

| CN | 1098859 A | * | 2/1995 |
| CN | 101095769 A | * | 1/2008 |
| EP | 1495764 A1 | | 1/2005 |
| JP | 095452 | | 4/1997 |
| JP | 103929 | | 4/2001 |
| JP | 315409 | | 11/2004 |
| WO | 2006/029577 A1 | | 3/2006 |
| WO | 2007/090289 A1 | | 8/2007 |

OTHER PUBLICATIONS

DWPI 2000-328347, Apr. 2000, DWPI, Wakat.*
Fukuda et al., Two New Monoterpene glycosides from Ku-Ding-Cha. Inhibitors of Acyl-CoA: Cholesterol Acyltransferase (ACAT), Chem. Pharm. Bull. 44(11) pp. 2173-2176, Nov. 1996.
Kong et al., "Berberine is a novel cholesterol-lowering drug working through a unique mechanism distinct from statins", Nature Medicine, 10, 1344-1351, Nov. 7, 2004 (Abstract).
Lau et al., "Anti-oxidative, anti-inflammatory and hepato-protective effects of *Ligustrum robustum*", Journal of Ethnopharmacology, vol. 83, Issues 1-2, Nov. 2002, pp. 63-71 (Abstract).
Intellectual Property Office of New Zealand; Examination Report, Apr. 14, 2011, pp. 1-2.
Abidi P, Chen W, Kraemer FB, Li H, Liu J. 2006. The medicinal plant goldenseal is a natural LDL-cholesterol agent with multiple bioactive components and new action of mechanisms. J. Lipid Res. 47: 2134-2147.
Anis KV, Kuttan G, Kuttan R. 1999. Role of berberine as an adjuvant response modifier during tumor therapy in mice. Phar. Pharmacol. Comm. 5: 697-700.
Arad Y, Ramakrishnan R, Ginsberg HN. 1992. Effects of lovastatin therapy on very-low-density lipoprotein triglyceride metabolism in subjects with combined hyperlipidemia: evidence for reduced assembly and secretion of triglyceride-rich lipoproteins. Meatbolism. 41: 487-493.
Asai T, Takeuchi T, Diffenderfer J, Sibley LD. 2002. Identification of small-molecule inhibitors of nucleoside triphosphate hydrolase in *Toxoplasma gondii*. Antimicrob Agents Chemother. 46: 2393-9.
Bays H. 2006. Statin safety: an overview and assessment of the data—2005. Am. J. Cardiol. 97(8A): 6C-26C.
Brusq J, Ancellin N, Grondin P, Guillard R, martin S, Saintillan Y. et al. 2006. Inhibition of lipid synthesis through activation of AMP-kinase: an additional mechanism for the hypolipidemic effects of berberine. J. Lipid Res. 47: 1274-1280.
Choi SW, Hur NY, Ahn SC, Kim DS, Lee JK, Kim DO, Park SK, Kim BY, Baik MY. 2007. Isolation and structural determination of squalene synthase inhibitor from *Prunus mume* fruit. J Microbiol Biotechnol. 17(12): 1970-5.
Chung MY, Rho MC, Lee SW, Park HR, Kim K, Lee IA, Kim DH, Jeune KH, Lee HS, Kim YK. 2006. Inhibition of diacylglycerol acyltransferase by betulinic acid from *Alnus hirsuta*. Planta Med. 72(3): 267-9.
Etheridge AS, Black SR, Patel PR, So J, Mathews JM. 2007. An in vitro evaluation of cytochrome P450 inhibition and P-glycoprotein interaction with goldenseal, *Ginkgo biloba*, grape seed, milk thistle, and ginseng extracts and their constituents. Planta Med. 73: 731-741.
Gugliucci A, Stahl AJ. 1995. Low-density lipoprotein oxidation is inhibited by extracts of *Ilex paraguariensis*. Biochem. Mol. Bio. Iterations. 35: 47-56.
Gugliucci A. 1996. Antioxidant effects of *Ilex paraguariensis*: Induction of decreased oxidability of human LDL in vivo. Biochem. Biophys. Res. Comm. 224: 338-344.

(Continued)

*Primary Examiner* — Terry A McKelvey
*Assistant Examiner* — Randall Winston
(74) *Attorney, Agent, or Firm* — Quarles & Brady LLP

(57) ABSTRACT

A medicinal combination of herbs, herbal extracts, and their chemical constituents that is synergistically effective for promoting human and veterinary health. The combination is a blood lipid level lowering synergistic composition comprising Ku ding cha, berberine or a berberine-containing plant extract, and other optional active ingredients. Methods of extraction and combination in synergistic amounts are also disclosed. The compositions according to the present invention may be used to treat or reduce the chance of contracting or the progression of a number of diseases or conditions in a subject, particularly cardiovascular diseases.

25 Claims, 21 Drawing Sheets

(56) References Cited

OTHER PUBLICATIONS

Hamilton-Craig I. 2001. Statin associated myopathy. Med. J. Aust. 175(9): 486-489.
He Z, Ueda S, Akaji M, Fujita T, Inoue K, Yang C. 1994. Monoterpenoid and phenylethanoid from *Ligustrum pedunculare*. Phytochemistry. 36 : 709-716.
Huang C, Zhang Y, Gong Z, Sheng X, Li Z, Zhang W. et al. 2006. Berberine inhibits 3T3-L1 adipocyte differentiation through the PPAR ÿ pathway. Biochem. Biophys. Res. Comm. 348: 571-578.
Im K, Jeong T, Kwon B, Baek N, Kim s, Kim DK. 2006. Acyl-CoA: Cholesterol Acyltransferase inhibitors from *Ilex macropoda*. Arch. Pharm. Res. 29; 191-194.
Jun T, Zhang H, Sun H, Pan L, Pin Y, Chen D. 1998. Monoterpenoid glycosides from *Ligustrum robustum*. Phytochemistry 48: 1013-1018.
Lee TK, Poon RT, Wo JY, Ma S, Guan XY, Myers JN, Altevogt P, Yuen AP. 2007. Lupeol suppresses cisplatin-induced nuclear factor-kappaB activation in head and neck squamous cell carcinoma and inhibits local invasion and nodal metastasis in an orthotopic nude mouse model. Cancer Res. 67(18):8800-9.
Lee WS, Im KR, Park YD, Sung ND, Jeong TS. 2006. Human ACAT-I and ACAT-2 inhibitory activities of pentacyclic triterpenes from the leaves of *Lycopus lucidus* TURCZ. Biol Pharm Bull. 29(2):382-4.
Leon C, Hill JS, Wasan KM. 2005. Potential role of acyl-coenzyme A: cholesterol transferase (ACAT) inhibitors as hypolipidemic and antiatherosclerosis drugs. Pharm. Res. 10: 1578-1588.
Negishi O, Negishi Y, Yamaguchi F, Sugahara T. 2004. Deodorization with Ku-ding-cha containing a large amount of caffeoyl quinic acid derivatives. J. Agric. Food Chem. 52: 5513-5518.
Nishimura K, Fukuda T, Miyase t, Noguchi H, Chen X. 1999. Activity-guided isolation of triterpenoid Acyl Coa Cholesteryl Acyl Transferase (ACAT) inhibitors from *Ilex kudincha*. J. Nat. Prod. 62: 1061-1064.
Nishimura K, Miyase T, Noguchi H. 1999b. Triterpenoid saponins from *Ilex kudincha*. J. Nat. Prod. 62: 1128-1133.
Novotny L, Vachalkova A, Biggs D. 2001. Ursolic acid: an antitumorigenic and chemopreventive activity. Minireview. Neoplasma. 48(4):241-6.
Ouyang M, Wang H, Chen Z, Yang C. 1996. Triterpenoid glycosides from *Ilex kudincha*. Phytochemistry. 43: 443-445.
Ouyang M, Yang C, Wu Z. 2001. Triterpenoid saponins from the leaves of *Ilex kudincha*. J. Asian Nat. Products Res. 3: 31-42.
Patocka, J. 2003. Biologically active pentacyclic triterpenes and their current medicine signification. J. Appl. Biomed. 1: 7-12.
Rajendran S, Deepalakshmi PD, Parasakthy K, Devaraj H, Devaraj SN. 1996. Effect of tincture of Crataegus on the LDL-receptor activity of hepatic plasma membrane of rats fed an atherogenic diet. Atherosclerosis. 123:235-41.
Raza JA, Babb JD, Movaheed A. 2004. Optimal management of hyperlipidemia in primary prevention of cardiovascular disease. Int. J. Cardiol. 97: 355-366.
Reihner E, Rudling M, Stahlberg D, Berglund L, Ewerth S, Bjorkhem I. et al. 1990. Influence of pravastatin, a specific inhibitor of HMG-CoA reductase, on hepatic metabolism of cholesterol. N. Engl. J. Med. 323: 224-228.
Sorci-Thomas M, Hendricks CL, Kearns MW. 1992. HepG2 cell LDL receptor activity and the accumulation of apolipoprotein B and E in response to docosahexaenoic acid and cholesterol. J. Lipid Res. 33: 1147-1156.
Staudt M, Mandl N, Joffre r, rambal S. 2001. Intraspecific variability of monoterpene composition emitted by *Quercus ilex* leaves. Can. J. For. Res. 31: 174-180.
Stein FLP, Schmidt B, Furlong EB, Soares LAS, Soares MCF, Vaz MRC, Baisch ALM. 2005. Vascular responses to extractable fractions of *Ilex paraguariensis* in rats fed standard and high-cholesterol diets. Biol. Res. Nurs. 7: 146-156.
Tang L, Jiang Y, Chang H, Zhao M, Tu P, Cui J et al. 2005. Triterpene saponins from the leaves of *Ilex kudincha*. J. Nat. Prod. 68: 1169-1174.
Thrift RN, Forte TM, Cahoon BE, Shore VG. 1986 Characterization of lipoproteins produced by the human liver cell line, Hep G2, under defined conditions. J. Lipid Res. 27: 236-241.
Wang SS, Chen JH, Liu XJ. 1994. Preliminary study on pharmacologic action of *Ligustrum japonicum*. Zhongguo Zhong Xi Yi Jie He Za Zhi. 14: 670-972 (article in Chinese).
Wu GY, Wu CH, Rifici VA, Stocked RJ. 1984. Activity and regulation of low density lipoprotein receptors in a human hepatoblastoma cell line. Hepatology 4(6): 1190-1194.
Zollner 1999 handbook of enzyme inhibitors, Wiley-VCH, Weinheim, Germany. p. 2815.
Office Action issued Jul. 21, 2011 on Chinese Patent Application No. 200980125115.0.
Office Action issued Nov. 7, 2011 on Chinese Patent Application No. 200980125115.0.
Office Action issued Nov. 30, 2011 on Canadian Application No. 2,723,132.
Office Action issued Mar. 5, 2012 on Mexican Patent Application No. MX/a/2010/011777.
Dharmananda, S., "Ku Ding Cha," itmonline.org, pp. 1-5, Dec. 2002, www.itmonline.org/arts/kundingcha.htm.
European Search Report, Sep. 19, 2012, Application No. 09738471.3-2107/ 2300028 PCT/IB2009005461.
Search & Examination Report for Singapore Patent Application No. 201007936-6 dated May 15, 2012.
Office Action issued Aug. 1, 2011 on Canadian Patent Application No. 2,723,132.
Office Action issued May 14, 2013 on Canadian Patent Application No. 2,723,132.
Office Action issued May 30, 2012 on Australian Patent Application No. 2009241274.
Office Action issued Jun. 13, 2012 on Chinese Patent Application No. 200980125115.0.
Office Action issued Dec. 4, 2012 on Chinese Patent Application No. 200980125115.0.
Office Action issued Aug. 28, 2013 on Japanese Patent Application No. 2011-506794.
Office Action issued Mar. 11, 2013 on Mexican Patent Application No. MX/a/2010/011777.
Office Action issued Jul. 31, 2013 on Mexican Patent Application No. MX/a/2010/011777.

\* cited by examiner

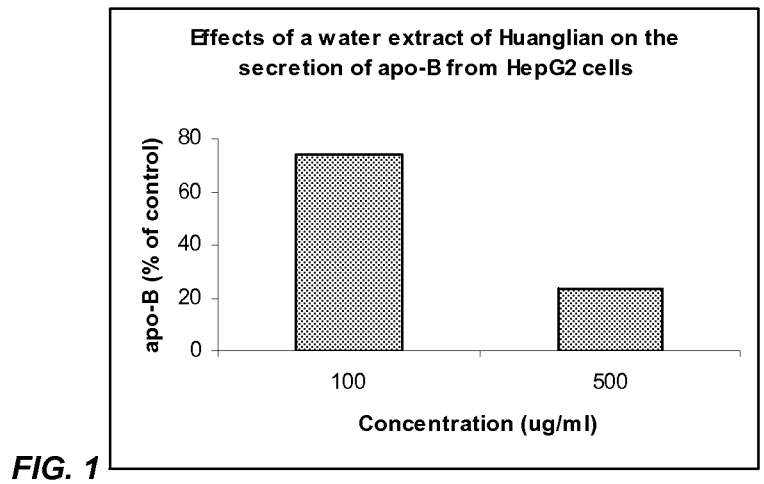
FIG. 1
FIG. 2
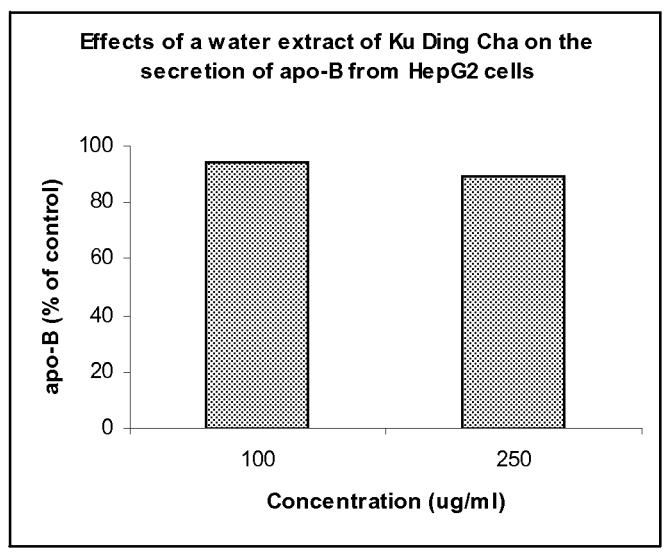

SYNERGISTIC PHARMACEUTICAL COMPOSITION, METHOD OF MAKING SAME AND USE OF SAME

FIELD OF THE INVENTION

The invention relates to medicinal compositions, particularly to combinations of herbs, herbal extracts and their chemical constituents for promoting human and veterinary health, particularly cardiovascular health.

BACKGROUND OF THE INVENTION

Cardiovascular disease (CVD) is the leading cause of death in most industrialized nations of the world. In the United States alone, 61 million people comprising approximately 25% of the total population have been reported to suffer from some type of CVD. Reducing the levels of blood cholesterol, in particular the low-density lipoprotein cholesterol, is known to be one of the effective strategies for the prevention of CVD [1].

A class of drugs, called statins, has been found to be highly effective in the reduction of blood cholesterol levels. Statins work by suppressing the activity of HMG-CoA reductase, the rate limiting enzyme in the synthesis of cholesterol in cells. The resultant decrease in intracellular concentrations results in a compensatory up-regulation of surface low-density lipoprotein (LDL) receptors, which in turn mediates clearance of LDL-cholesterol from plasma. Clinically, HMG-CoA reductase inhibitors are effective in lowering blood LDL-cholesterol levels by 20-40% and have also been found to be effective in reducing the levels of triglyceride and inducing modest increases in the levels of HDL-cholesterol in blood [2,3]. Despite their success in the management of blood lipid concentrations, statin therapy however cannot be prescribed to all patients with hyperlipidemia. In particular, these drugs are contraindicated in patients with cholestasis or impaired hepatic functions. In some patients, statins have also been reported to cause elevations in various hepatocellular enzymes such as creatine kinase. Statins have also been found to have potential adverse effects on muscle, kidney and the nervous system of some patients. There have also been reports of myopathy during the treatment with statins. Although myopathy occurs in only 0.1 to 0.2% of patients receiving statins, its risk increases with the increase in dose. In addition, if left untreated, myopathy could lead to a more serious and life-threatening condition called rhabdomylosis. Consequently, following the development of myopathy immediate cessation of statin therapy is required [4,5].

Treatment of hypercholesterolemic patients with berberine (BBR) at a dose of 1 g/day for 3 months was found to reduce serum cholesterol concentrations by 29%, triglycerides by 35% and LDL-cholesterol by 25% [6]. Experimental studies also support the cholesterol-lowering efficacy of BBR. Oral administration of BBR to hyperlipidemic hamsters at a dose of 100 mg/day for 2 weeks was found to reduce serum total- and LDL-cholesterol levels by up to 30% [6-8]. A number of in vitro studies utilizing human hepatoma cell lines such as Hep G2 cells have also been carried out to determine the underlying mechanisms of cholesterol-lowering effects of BBR. Results from these studies indicate that BBR increases the expression of LDL receptors in the cells through a post-transcriptional mechanism that increases the stabilization of mRNA for these receptors. BBR was also found to inhibit the synthesis of cholesterol and triglyceride in the cells through activation of an AMP-activated protein kinase [6-8]. In a more recent study, BBR was found to inhibit differentiation of 3T3-L1 adipocytes and to inhibit lipogenesis in the cells through PPAR pathways [9].

Although evidence from a number of studies indicates that BBR has cholesterol-lowering properties, a dose of approximately 1 g/day appears to be required to achieve clinical benefits. Safety of chronic administration of this dosing remains a concern. In an experimental study, intra-peritoneal administration of BBR at doses exceeding 15 mg/Kg for 10 days to mice was found to be lethal to the animals [10]. Higher doses of BBR were also found to be toxic to cells in culture. For example, treatment of L929 cells with BBR in doses greater than 40 µg/ml was found to induce cytotoxicity. More recently, incubation of human liver microsomes with BBR at concentrations of 20 µM was found to decrease the activities of various CYP 450 enzymes including CYP2D6, CYP3A4 and CYP2E1 [11].

An herbal tea, Ku Ding Cha (also referred to as Kudingcha, Kuding tea, bitter tea, ku cha), is also known to have cardiovascular benefits. It is widely consumed in China as a normal tea or functional drink. The original plant of Ku Ding Cha consists of about 10 most commonly known species in the genus *Ligustrum, Oleaceae*, and *Ilex, Aquifoliaceae* including *Ligustrum pedunclare, Ligustrum purpurascens, Ligustrum japonicum, Ligustrum robustrum, Ilex cornuta, Ilex kudincha* C. J. Tseng (*Aquifoliaceae*), *Ilex latifolia, Cratoxylum prunifolium, Ehretia thyrsiflora, Photinia serruiata* [12] and *Ilex paraguariensis*. The extract from these ground plants in hot water is consumed as a tea. In animal studies extracts of some of these species have been found to promote circulation of blood, lower blood pressure, have anti-oxidative effects and reduce levels of lipids in plasma [13-15]. For example, in an experimental study daily gavaging of water extracts of *Ilex paraguariensis* to hypercholesterolemic rats at a dose of 500 mg/day for 2 weeks was found to significantly reduce the plasma concentrations of cholesterol and triglycerides [16]. In another study, daily administration of extracts of *Ligustrum japonicum* for 1-3 months reduced the levels of blood total cholesterol in hypercholesterolemic rabbits [17]. The clinical benefits of the tea in the management of human blood cholesterol concentrations however have not been determined.

The biologically active components of Ku Ding Cha have yet to be determined. Aqueous and alcoholic extracts of leaves of various *Ilex* species contain numerous terpenoids, flavonoids [18-23], triterpenes, phenylethanoid glycosides, caffeoyl quinic acid and derivatives thereof. Some of these compounds are implicated in the cholesterol-lowering effects of Ku Ding Cha; recent studies have found that a number of mono- and tri-terpenes isolated from the leaves and twigs of two species of Ku Ding Cha including *Ilex kudingcha* and *Ilex macropoda* were found to inhibit the activity of acyl-CoA: cholesterol acyltransferase (ACAT) in vitro [24-27]. ACAT activity is important for regulation of cholesterol absorption from the gut and esterification of cholesterol with fatty acids in mammals. Inhibition of ACAT in hepatocytes has been shown to decrease the secretion of apolipoprotein-B containing lipoproteins, such as very low density lipoprotein (VLDL) particles from the liver [28].

Many of the triterpenoid saponins have been isolated from *Ilex kudingcha*: ilekudinosides A-S, ilexoside XL VIII, cynarasaponin C, latifolosides A, C, G and H, kudinoside G. Some of them exhibited significant ACAT inhibitory activity [26].

Some monoterpenoid and phenylethanoid glycosides have also been isolated from Ku Ding Cha (*Ligustrum pedunculare*) leaves: lipedosides A-I and A-II as phenylthanoid glycosides, and lipedosides B-I, B-II, B-III, B-IV, B-V, and B-VI as monoterpenoid glycosides. Lipedoside B-III has been identified as inhibitor of ACAT with $IC_{50}$ of 269 µM [23]

Ku Ding Cha is also known to contain ursolic acid, betulin, lupeol, and chlorogenic acid.

Ursolic acid (3β-Hydroxy-12-ursen-28-ic acid), has been identified as an inhibitor of several enzymes, including adenosine deaminase, arachidonate lipoxygenase, aromatase, cyclooxygenase, DNA ligase I, elastase, protein kinases A and C, and RNA-directed DNA polymerase [29]. Recently, ursolic acid has also been identified as an inhibitor of nucleoside triphosphate hydrolase (NTPase, $IC_{50}$ 0.6 µM) and acyl-CoA: cholesterol acyltransferase (ACAT, $IC_{50}$, 58.8 µM) [30-31]. Ursolic acid is also a strong antitumorigenic and chemopreventive agent [32].

Betulin (lup-20[29]-ene-3β,28-diol) and betulinic acid (3-hydroxy-20[29]-lupen-28-oic acid) are anti-inflammatory and cytotoxic against a variety of tumor cell lines [33]. U.S. Pat. No. 5,679,828 has found that betulinic acid and its derivatives have strong anti-HIV infection activity. Betulinic acid has also been identified as an inhibitor of acyl CoA: diacylglycerol acyltransferase (DGAT, $IC_{50}$, 9.6 µM) [34]. Furthermore, betulin and betulinic acid are good ACAT inhibitors with $IC_{50}$ of 83 and 16.2 µM, respectively [24].

Lupeol (3β-Hydroxy-20(29)-lupene, or 20(29)-Lupen-3β-ol) has been found to have anti-cancer activity via down-regulation of NF-kB and has been identified as an inhibitor of acyl-CoA: cholesterol acyltransferase (ACAT $IC_{50}$, 48 µM) [24,35].

Chlorogenic acid, a chemical component of Ku Ding Cha, has been identified as squalene synthase inhibitor, with an $IC_{50}$ of 0.1 µM [36].

Hawthorn, a plant cultivated widely in Europe and China (called shanzha in China), has been found to have various health-promoting properties. In Europe, the species of hawthorn which are commonly accepted in herbal medicine include *Crataegus oxyacantha, Crataegus pentagyna Waldst, Crataegus nigra Waldst, Crataegus azarolus* L. and *Crataegus monogyna*. In China, two other varieties of hawthorn including *Crataegus pinnatifida* and *Crataegus pinnatifida* Bge var. *major* NE Br., have been used in traditional Chinese medicine. Studies indicate that both European as well as Chinese varieties have various health benefits including antioxidant, anti-inflammatory and hypolipidemic effects. These varieties have also been found to have protective effects on the brain and vascular endothelium and endothelium-dependent relaxation. In addition, some clinical studies also indicate that hawthorn has blood pressure lowering properties and is effective in the treatment of mild forms of arrhythmia. Flavonoids, in particular proanthocyanidines are believed to be the active components of hawthorn. Studies utilizing various flavonoids indicate that these compounds possess cholesterol-lowering properties and more specifically they have been found to increase the hepatic uptake of cholesterol [37].

SUMMARY OF THE INVENTION

The present inventors have found that certain compositions comprising huanglian and Ku Ding Cha, as herbs, extracts or chemical combinations thereof, can synergistically promote cardiovascular health. The synergistic combination can be obtained either through extracting one or more herbs together or extracting each herb separately and then combining the extracts; the latter method is preferred. The present inventors have also discovered that berberine and berberine related alkaloids, e.g. palmitine chloride, that are found within the huanglian extract, interact synergistically with each other to promote cardiovascular health. Naturally- or synthetically-derived chemical constituents may be used to make the synergistic combinations effective for promoting cardiovascular health.

Ku Ding Cha and its extracts can be obtained from any part of the fresh or dried plant, whole leaves or milled powder by using liquid extraction, or supercritical fluid extraction, or high-pressure extraction using conventional liquid solvents and combined with small amounts of supercritical fluids, although liquid extraction from finely ground powder of dried KDC leaves is preferred. The most preferred species of Ku Ding Cha is derived from *Ilex kudingcha*, although the species *Ilex aquifoliacese, Ilex latifolia* Thunb, *Ligustrum robustum, Ehretia thyrsiflora, Clerodendrum fortunatum* L. and *Ilex cornuta* Lindl. ex paxt. also show the same synergistic effect. Suitable solvents for liquid extraction include water, acidic water, water-alcohol mixtures, water-lower alkyl($C_{1-6}$) alcohol mixtures, alcohols, especially lower alkyl($C_{1-6}$) alcohols, esters, especially $C_{2-10}$ esters, ethers, especially $C_{4-12}$ ethers, hydrocarbon chlorides or other organic solvents or mixtures thereof. Water, alcohol, ethyl acetate and ethyl acetate-based solvent mixtures are preferred, although an alcoholic extraction is most preferred. Extraction can be carried out by using liquid extraction, including pressurized liquid extraction (PLE, also called accelerated solvent extract, ASE), maceration, sonication, microwave assist extraction or supercritical fluid extraction, soaking, agitation, or supersonic aid extraction in a proportion e.g. 1 ml-1 Litre, preferably 2-500 ml, more preferably 2-200 ml, more preferably 2.5-50 ml, most preferably 10 ml of solvent per gram of finely ground powder of Ku Ding Cha, most preferably obtained from the leaf, for a time between e.g. one minute to 100 hours, preferably 2 minutes to fifty hours, more preferably 5 minutes to twenty-four hours, even more preferably for 20 minutes to 5 hours, most preferably 2 hours, depending on the chosen extraction procedure. The extractions were carried out at a temperature of about 4-120° C., or preferably 15-100° C., or more preferably 30-90° C., or more preferably 50-80° C., or even more preferably 60-80° C., most preferably 70-78° C., or even most preferably at 78° C., in the high-pressure container and/or under reflux conditions, followed by cooling to room temperature and reducing the pressure to atmospheric state, then separating of the Ku Ding Cha extract solution from the solid phase by filtration, centrifugation, or subside and decant or other separation techniques. Filtration is the preferred method of separation. The resulting solutions can be concentrated to liquid or solid products through evaporation at a temperature of 20 to 80° C., preferably 20 to 50° C., more preferably 30 to 40° C., and most preferably 30° C., by freeze-drying preferably, although concentration may also occur by using an evaporator or spray-drying techniques.

Ku Ding Cha includes any part of a Ku Ding Cha plant, its extracts, chemically synthesized compounds that are found in Ku Ding Cha, or pure chemical species identified from any part of the fresh or dried plant, and will hereinafter, including in the claims, be referred to as KDC. KDC has been found to contain multiple active ingredients in apoB secretion lowering tests, and also has a synergistic effect in combination with huanglian and its extracts. A few of the active ingredients from KDC were identified as tri-terpenes: lupeol, ursolic acid, betulin and betulinic acid and related derivatives; a group of tri-terpenoid saponins; a group of mono-terpenoid glycosides, a group of phenylethanoid glycosides, caffeoyl quinic acids and their derivatives. These compounds may also be isolated from a variety of other plants. Plant species with the highest content of ursolic acid include, but are not limited to, Greek Sage (*Salvia triloba* L.), Oleander (*Nerium olean-* der L.) and Rosemary (*Rosmarius officinalis* L.). Plant species with the highest content of betulin and betulinic acid include, but are not limited to, bark of *Betula alba*, *B. pendula*, *B. platyphylla* and seed of *Ziziphus vulgaris* var. *spinosus*, bark of birch. Plant species with the highest content of lupeol include, but are not limited to, *Alnus glutinosa*, *Aloe vera*, *Apocynum cannabinum* and *Arbutus unedo*. Chlorogenic acid can also be isolated from coffee, black tea or *Eucommia* bark (Du zhong, *Eucommia ulmoides* Oliv.).

Huanglian and its extracts, chemically synthesized compounds that are found in Huanglian, berberine and berberine containing extracts, berberine-derivatives, analogs, and berberine related alkaloids will hereinafter, including in the claims, be referred to as HL. Huanglian, berberine and berberine-related alkoloids such as palmitine chloride are most preferably obtained from *Coptis chinensis Franch* by using liquid extraction from the dried and powdered herb. *Coptis chinensis* is also sometimes known as *Coptis* root, Golden Thread, Goldthread, Huang Lian, Huanglian, *Rhizoma Coptidis*, or *Coptis chinensis* rhizomes. HL may also be preferably obtained from *Coptis deltoidea* C Y. Cheng et Hsiao and *Coptis teeta* Wall. Furthermore, berberine, berberine-derivatives, analogs, and berberine related alkaloids may also be found in a variety of plants, including goldenseal (*Hydrastis canadensis*), San-Ke-Zhen (*Berberis* spp.) *Berberis pratti*, *Schnneid*, *Berberis sargentiana Schneid.*, *Berberis virgetorum Schneid.*, *Berberis vernae Schneid.*, *Berberis soufleana. Schneid. Berberis pruinosa Franch.*, *Berberis poiretti Schneid.*, *Berberis wilsonae Heml.*, *Berberis dictyophylla*, *Fr.*, *Berberis julianae Schreid.*, *Berberis jamesiana Forrest et W. W. Sm.*, *Berberis heteropoda Schrenk.*, *Berberis brachypoda Maxi*, *Berberis sargentiana*, *Berberis thunbergii*, *Berberis vulgaris* (barberry), and Oregon grape (*Berberis aquifolium*) as well as *Corydalis Tuber* (Yan hu suo), *Coptis japonica*, *Coptis Trifolia*, *Coptis teeta*, *Coptis quiquefolia*, *Coptis deltodea*, *Phellodendron amurence* (Amur cork tree or Huang bai), *Argemone mexicaca* L. (prickly poppy), *Andira inermis* (cabbage bark), *Corydalis* Spp (Fumewort), *Mahonia aquifolium* (blue barberry), *Chelidinium majus* L. (Celandine), *Menispermum canadense* L. (moonseed), *Tinospora Cordifolia* (Guduchi), and *Eschscholzia californica* (California poppy). Suitable solvents include water, acidic water, water-alcohol mixtures, acid water-alcohol mixtures, water-lower alkyl($C_{1-6}$) alcohol mixture, acid water-lower alkyl ($C_{1-6}$) alcohol mixture, alcohol, especially lower alkyl($C_{1-6}$) alcohol, esters, especially $C_{2-10}$, ester, ethers, especially $C_{4-12}$ ether, hydrocarbon chlorides or other organic solvents or mixture thereof. Water, acid water, aqueous alcohol, acidic aqueous alcohol, ethyl acetate and ethyl acetate-based solvent mixture are preferred, although an aqueous alcohol extraction is most preferred. Extraction can be carried out by using liquid extraction, including pressurized liquid extraction (PLE, also called accelerated solvent extraction, ASE), maceration, sonication, microwave assist extraction or supercritical fluid extraction, soaking, agitation, supersonic aid extraction, in a proportion e.g. 1 ml-1 Litre, preferably 2-500 ml, more preferably 2 ml-200 ml, more preferably 2.5-50 ml, most preferably 10 ml of solvent per gram of *Coptis chinensis* milled powder for a time between e.g. one minute to 100 hours, preferably 2 minutes to fifty hours, more preferably 5 minutes to twenty-four hours, even more preferably for 20 minutes to 5 hours, most preferably 2 hours, at a temperature e.g. 4-120° C., preferably 15-100° C., more preferably 30-90° C., more preferably 50-80° C., even more preferably 60-80° C., most preferably 70-78° C., most preferably at 78° C., in a high-pressure container and/or under reflux conditions; followed by cooling and reducing pressure to room temperature and atmospheric state, then separating of the *Coptis chinensis* solution from the solid phase by filtration, centrifugation, subside and decant, or other separation techniques. Filtration is the most preferred separation technique. The resulting solutions can be concentrated to liquid or solid extract products most preferably with freeze-drying, although evaporator or spray-drying techniques are also preferred.

Berberine and berberine related alkaloids found within the huanglian extract include, but are not limited to, berberine, and berberine-related or analog compounds, e.g. berberine sulfate, berberine chloride, palmatine chloride, coptisine chloride, worenine chloride, jatrorrhizine chloride, colchicines, magnoflorine, oxyberberine, dihydroberberine, (−)-canadine, β-hydrastine, hydrastinie, and salts thereof. Combinations of these alkaloids were found to have synergistic effects in lowering apoB secretion.

The invention further includes the use of compositions comprising KDC in combination with HL, further comprising at least one additional active ingredient selected from the group consisting of Gymnemic acid and Gymnemic acid containing extract from *Gymnema* (*Gymnema Sylvestre*), [Wu Xue Teng]; Gypenosides and Gypenosides containing extract from *Gynostemma pentaphyllum* (*Gynostemma pentaphylla* (thumb.) makino), [Jiao Gu Lan]; Isoflavones and Isoflavones containing extract from Puerariae (*Pueraria lobata* O.), [Ge Gan]; Flavones and Flavones containing extract from Hawthorn (*Crataegus pinnatifida*, and *pinnatifida* Bge. Var. *major* NE Br.), [Shan zha]; Diosgenine and Diosgenine containing extract from Wild Chinese Yam (*Dioscorea Opposita Thunb*), [Shan Yao]; Andrographolides and Andrographolides containing extract from *Andrographis* (*Andrographis paniculatae*), [Chuan Xin Lian]; orange peel and orange peel extracts; tangerine and tangerine peel extracts; hawthorn and/or hawthorn extracts; *Semen Cassiae* (Jue ming zi) and Semen extracts; *Rhizoma Alismatis* (ze xie) and *Rhizoma Alismatis* extracts; *Fructus Lycii* (Gou Qi Zi) and *Fructus Lycii* extracts; *Radix Glycyrrhizae* (gang cao) and *Radix Glycyrrhizae* extracts; *Radix Bupleuri* (cai hu) and *Radix Bupleuri* extracts; *Radix* et *Rhizoma Rhei* and *Radix* et *Rhizoma Rhei* extracts; Fleeceflower Root (shou wu) and Fleeceflower root extracts; *Semen Ziziphi Spinosae* (suan zao ren) and *Semen Ziziphi Spinosae* extracts; *Rhizoma Polygonati Odorati* (yu zhu) and *Rhizoma Polygonati Odorati* extracts; *Epimedium Herb* (yin yang huo) and *Epimedium Herb* extracts; *Radix Scrophulariae* (xuan shen) and *Radix Scrophulariae* extracts; *Radix Angelicae Sinensis* (dang gui) and *Radix Angelicae Sinensis* extracts; Ginseng and Ginseng extracts; *Rhizoma Curcumae Longae* (Jiang Huang) and *Rhizoma Curcumae Longae* extracts; *Ganoderma Lucidumseu Sinensis* (lingzhi); and *Ganoderma Lucidumseu Sinensis* extracts; *Cortex Eucommiae* (du zhong) and *Cortex Eucommiae* extracts; and *Fourstamen Stephania* Root and *Fourstamen Stephania* Root extract.

BRIEF DESCRIPTION OF THE DRAWINGS

FIG. 1. shows the dose-related effects of a water extract of HL on the secretion of apolipoprotein-B containing lipoproteins (apo-B) from Hep-G2 cells.

FIG. 2. shows the dose-related effects of a water extract of KDC on the secretion of apolipoprotein-B containing lipoproteins (apo-B) from Hep-G2 cells.

DETAILED DESCRIPTION OF THE INVENTION

Figure 3:
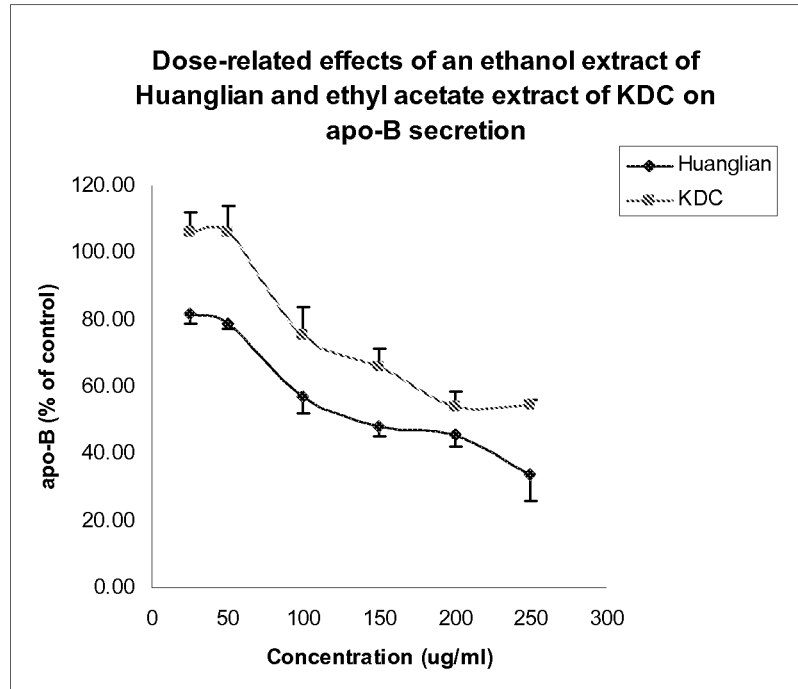
FIG. 3 shows the dose-related effects of an ethanol extract of HL and an ethyl acetate extract of KDC on the secretion of apolipoprotein-B containing lipoproteins (apo-B) from Hep-G2 cells.

Evidence from numerous studies indicates that berberine (BBR), an alkaloid isolated primarily from the herbs huanglian (*Coptis chinensis*) and goldenseal (*Hydrastis canadensis*), possesses cholesterol-lowering properties. In particular, berberine has been found to enhance expression of LDL receptors in liver cells through a post-transcriptional mechanism that apparently stabilizes the mRNA for the receptors. This increased expression of LDL receptors enhances the hepatic uptake of cholesterol, consequently resulting in lowering the levels of LDL-cholesterol in plasma.

The cholesterol-lowering properties of KDC extracts appear to be related to their content of terpenes, terpenoids, flavonoids, phenylethanoid glycosides, caffeoyl quinic acid and its derivatives. Recent studies have shown that these terpenoids inhibit a hepatic microsomal enzyme, ACAT, which is required for the esterification and secretion of cholesterol from liver cells.

Although berberine and KDC have been reported to possess cholesterol-lowering properties, they appear to act through different mechanisms. Without being held to any particular mechanism of action, berberine has been found to enhance the hepatic uptake of cholesterol whereas KDC has been reported to reduce the hepatic secretion of cholesterol. Cholesterol is transported to the tissues by LDL and apolipoprotein B (apo-B) is the primary apolipoprotein of LDL. High levels of apo-B can lead to atherosclerosis. The present invention relates to compositions comprising HL and KDC that have been found to act synergistically to lower apo-B secretion. The compositions are useful in their lipid lowering effects to promote human and veterinary health, particularly cardiovascular health and to prevent or treat cardiomyopathy.

The compositions according to the present invention may be used to treat or reduce the chance of contracting or the progression of a number of diseases or conditions in a subject. Diseases or conditions include, for example, cardiomyopathy, cardiovascular disease, hyperlipidemia, hyperlipoproteinemia, high levels of lipoprotein (a), ischemia, coronary heart disease, atherosclerosis, angina, cerebrovascular disease, stroke, overweight or obesity, metabolic syndrome, polycystic ovary syndrome, myocardial infarction, diabetes, insulin resistance, sclerotic disorder, hyperglycemia, hypertension, arrhythmia, diseases of the central nervous system, diseases of the brain, diseases of the peripheral nervous system and inflammation.

The invention also includes pharmaceutical compositions, comprising HL and KDC in combination with a pharmacologically acceptable carrier. Those of skill in the art are familiar with any pharmaceutically acceptable carrier that would be useful in this regard, and therefore the procedure for making pharmaceutical compositions in accordance with the invention will not be discussed in detail. Suitably, the pharmaceutical compositions may be in the form of tablets, capsules, liquids, lozenges, pastes, salves, powders, lotions, aerosol, solutions suitable for injection or suppositories.

The oral compositions can include an inert diluent or an edible carrier. For the purpose of oral therapeutic administration, compositions comprising HL and KDC can be incorporated with excipients and used in the form of tablets, troches, powders, or capsules, e.g., gelatin capsules. Oral compositions can also be prepared using a fluid carrier. Pharmaceutically compatible binding agents or other carrier materials can be included as part of the composition. Such binding agents and carriers can be a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent. HL and KDC compositions may also be admixed with a food or beverage and taken orally. Fortified foods and beverages may be made by adding HL and KDC during the manufacturing of the food or beverage. Alternatively, the consumer may add HL and KDC to the food or beverage near the time of consumption. Each ingredient may be added to the food or beverage together with the other ingredients or separately from the other ingredients. Examples of foods and beverages are, but not limited to, cereals, snack bars, dairy products, fruit juices, powdered food and dry powder beverage mixes.

The lipid level lowering composition according to the present invention can be administered by any suitable route including oral, aerosol, or other device for delivery to the lungs, nasal spray, intravenous, intramuscular, intraperitoneal, vaginal, rectal, and topical, transmucosal or transdermal. For transmucosal or transdermal administration, penetrants appropriate to the barrier to be permeated are used in the formulation. Such penetrants are generally known in the art. Transmucosal administration can be accomplished through the use of nasal sprays, suppositories or retention enemas for rectal delivery. The suppositories can include conventional suppository bases such as cocoa butter and other glycerides. For transdermal administration, the active compounds are formulated into ointments, salves, gels, or creams as generally known in the art.

HL and KDC may be administered simultaneously or sequentially over a period of time. The effective time range for administering HL and KDC sequentially is up to and including 60 minutes. Preferably, HL and KDC are co-administered. Compositions comprising HL and KDC may be used alone or in combination with another medicament.

Dosages of HL and KDC in accordance with the invention depend upon the particular condition to be treated, as well as the age, sex and general health condition of the patient. Effective dosages are administered in a synergistically effective amount of HL and KDC in amounts sufficient to produce a synergistic effect. However, suitable dosages may be found in the range between 0.1-500 mg/kg body weight per day, in between 1 and 10 daily doses. Preferably, effective dosages would range between 1-400 mg/kg body weight per day, administered in between 2 to 6 times a day in divided doses. More preferably, the effective dosage may be 2-100 mg/kg body weight per day, administered in between 2 to 4 times a day in divided doses. Most preferably, the effective dosage may be 10-60 mg/kg body weight per day, administered in 3 times per day in divided doses.

A HL:KDC weight ratio of about 1% to 99% is synergistic; however, 25% to 99% is preferable, 20% to 80% is more preferable, 25% to 75% is even more preferable; 33% to 75% is more preferable; and 40% to 67% is more preferable, and an approximately 1:1 ratio is most preferred.

A HL ethanol extract:KDC ethanol extract weight ratio of about 1% to 99% is synergistic and preferable; however, 25 to 75% more preferable, 30% to 67% is even more preferable; and an approximately 1:2 ratio is most preferred.

A HL ethanol extract:KDC ethyl acetate extract weight ratio of about 1% to 99% is synergistic and preferable; however, 25% to 75% is more preferable, 33% to 67% is even more preferable, and an approximately 2:1 ratio is most preferred.

A HL ethanol extract:KDC water extract weight ratio of about 1% to 99% is synergistic; however, 5% to 85% is preferable, 25% to 75% is more preferable, and an approximately 3:1 ratio is most preferred.

A HL ethanol extract:chlorogenic acid weight ratio of about 1% to 99% is synergistic; however, 25% to 75% is preferable, and an approximately 1:3 ratio is most preferred.

A berberine:lupeol weight ratio of about 1% to 65% is synergistic and preferable; however, 5 to 60% is more preferable, 30% to 55% is even more preferable, and an approximately 1:1 ratio is most preferred.

A berberine:betulin weight ratio of about 1% to 99% is synergistic and preferable; however, 30 to 70% is more preferable, 30% to 60% is even more preferable; and an approximately 1:1 ratio is most preferred.

A berberine:ursolic acid weight ratio of about 1% to 50% is synergistic and preferable; however, 1 to 49% is more preferable, 30 to 40% is yet more preferable; and an approximately 1:2 ratio is most preferred.

A berberine:chlorogenic acid weight ratio of about 1% to 75% is synergistic and preferable; however, 5 to 74% is more preferable, 20% to 50% is yet more preferable; and an approximately 1:3 ratio is most preferred.

A berberine:palmitine chloride weight ratio of about 1% to 99% is synergistic and preferable; however, 25% to 75% is more preferable; and an approximately 2:1 ratio is most preferred.

The terms "effective amount" and/or "therapeutic amount" means a dosage sufficient to provide prevention and/or treatment for the disease state being treated. This will vary depending on the patient, the condition disease and the treatment being effected. The patient may be human or animal, including birds and mammals. Thus, the composition has both medical and veterinarian uses.

In the Examples to follow, Apo-B secretion experiments were carried out on HepG2 cells. These cells were obtained from the American Type Culture Collection (cat #: ATCC HB-8065). HepG2, a human hepatoblastoma-derived cell line, is one of the most commonly used models to study lipoprotein uptake and metabolism in intact human liver. These cells secrete most of the plasma proteins secreted from human liver cells including apolipoprotein-B [38]. In addition, most of the enzymes involved in intra- and extracellular cholesterol metabolism including LCAT, ACAT, HMG-CoA reductase and Cholesterol 7-α-hydroxylase are expressed in these cells [39]. They also exhibit both saturable high-affinity and nonsaturable low-affinity LDL binding sites [40].

The invention will now be further elucidated by the following Examples.

EXAMPLE 1

Figure 4:
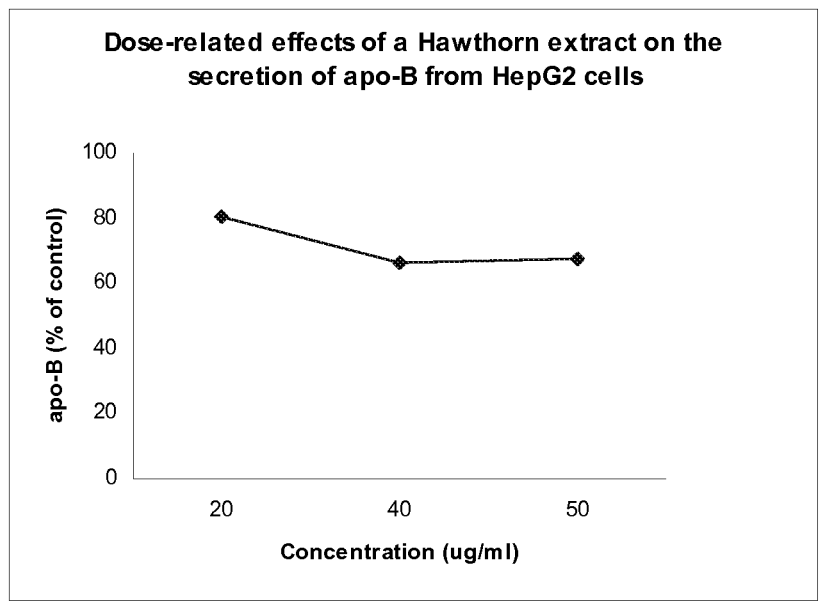
FIG. 4 shows the dose-related effects of a hawthorn extract on the secretion of apolipoprotein-B containing lipoproteins (apo-B) from Hep-G2 cells.
Figure 5:
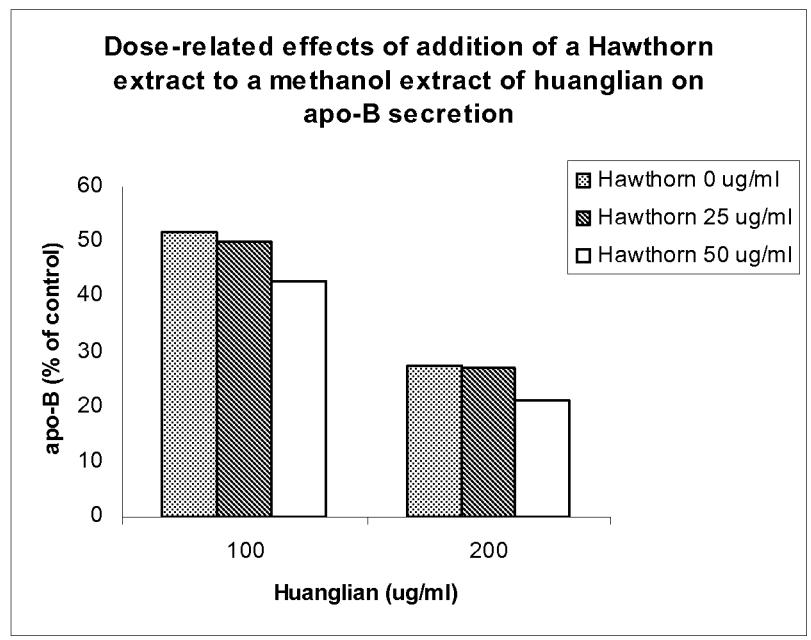
FIG. 5 shows the dose-related effects of addition of a hawthorn extract to a methanol extract of HL on the secretion of apolipoprotein-B containing lipoproteins (apo-B) from Hep-G2 cells.
Figure 6:
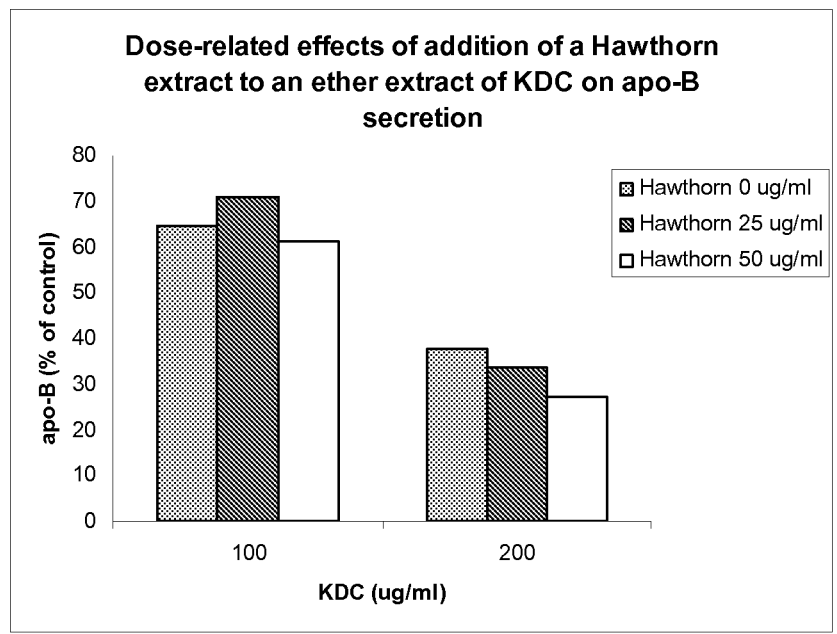
FIG. 6 shows the dose-related effects of addition of a hawthorn extract to an ether extract of Ku Ding cha (KDC) on the secretion of apolipoprotein-B containing lipoproteins (apo-B) from Hep-G2 cells.

Determining the Dose Related Effects of HL and KDC on the Secretion of Apo-B from HepG2 Cells The effects of HL, KDC and hawthorn extracts, when used in isolation as well as in combination, on the secretion of apo-B from human hepatoma cells, Hep-G2 was determined. Water extracts of *Coptis chinesis* (Huanglian) and Ku Ding Cha (*Ilex kudingcha*) were developed and tested; results are indicated in FIGS. 1 and 2, respectively. Ethanolic extracts of *Coptis chinesis* (Huanglian) and ethyl acetate extracts of Ku Ding Cha (*Ilex kudingcha*) were also developed and hawthorn extract was used for these experiments shown in FIGS. 3-12. Isolated huanglian or Ku Ding Cha extracts reduce the secretion of apo-B from Hep-G2 cells in a dose-related manner (FIG. 3) and the hawthorn extract also has an inhibitory effect on the secretion of apo-B from the cells (FIG. 4). HL had greater efficacy than KDC. The $IC_{50}$ values for HL and KDC extracts were found to be 146 μg/ml and 238.6 μg/ml, respectively. The addition of hawthorn extract to the HL (FIG. 5), as well as to KDC (FIG. 6), was found to increase the efficacy of both extracts in a dose-dependent manner.

Further, the effect of combining HL and KDC extracts in the weight ratio of 1:1 on the secretion of apo-B (FIG. 8) indicates synergism. As is apparent, the combination was found to have greater efficacy than isolated extracts of either HL or KDC, thus indicating synergism between the extracts.

EXAMPLE 2

Figure 7:
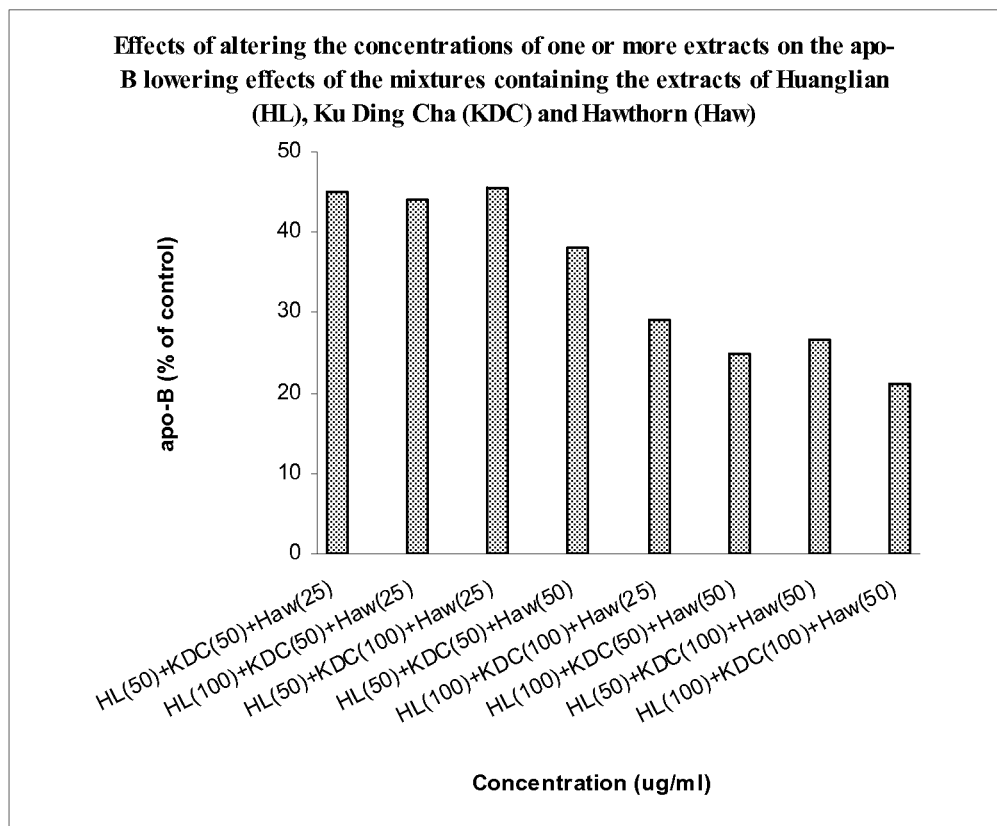
FIG. 7 shows the dose-related effects of mixtures of HL, KDC and hawthorn (Haw) extracts on the secretion of apolipoprotein-B containing lipoproteins (apo-B) from Hep-G2 cells.
Figure 8:
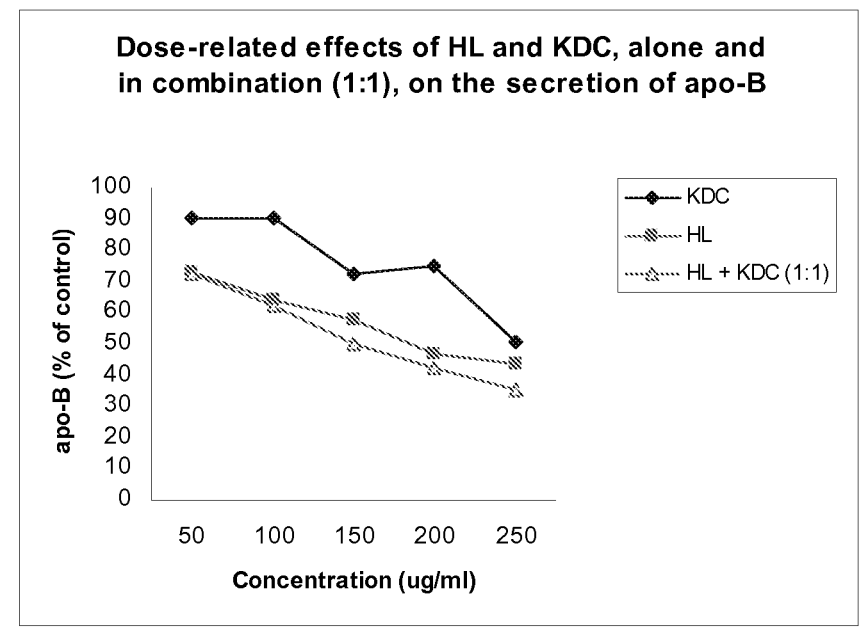
FIG. 8 shows the dose-related effects of an ethanol extract of HL and an ethyl acetate extract of KDC, both separately and in a 1:1 ratio combination with each other, on the secretion of apolipoprotein-B containing lipoproteins (apo-B) from Hep-G2 cells.

Determining the Dose Related Effects of HL, KDC and Hawthorn on the Secretion of Apo-B from HepG2 Cells The effects of mixtures containing HL, KDC, and hawthorn extracts, at two different concentrations, on the secretion of apo-B are shown (FIG. 7). In the presence of hawthorn, increasing the concentrations of either HL or KDC alone had little additional effect on the inhibitory effects of the mixture on apo-B secretion, whereas increasing the concentration of hawthorn was found to increase the overall efficacy of the combined extract. However, when the concentrations of any two of these three extracts were increased simultaneously, the overall efficacy of the mixture was found to be increased. Increasing the concentration of all three extracts was found to have the greatest efficacy. Factorial analysis of the data revealed that among the three extracts, hawthorn extract contributed the most to the overall efficacy of the mixture, followed by HL and KDC had a minimal effect. The nature of interaction between HL and KDC was found to be synergistic.

EXAMPLE 3

Determining the $IC_{50}$ Values for Combinations of HL and KDC Extracts

The $IC_{50}$ values for HL and KDC were found to be 146 ug/ml and 239.1 ug/ml, respectively. When the concentration of HL was kept constant at 50 ug/ml and KDC varied, the $IC_{50}$ value was found to be 163.5 ug/ml; this result indicates that 113.5 ug/ml of KDC extract should be added to 50 ug/ml HL for 50% efficacy. Furthermore, with HL concentration constant at 100 ug/ml and KDC varied, the $IC_{50}$ was found to be 123.3 ug/ml. Thus, 100 ug/ml of HL should be added to 23.3 ug/ml of KDC extract for 50% efficacy. The lower $IC_{50}$ values of the combined extracts suggest that the two extracts acted synergistically in lowering the secretion of apo-B from hepG2 cells.

Additional experiments were subsequently carried out to confirm the synergism between the HL and KDC extracts. Three commonly used approaches including non-linear blending, isobologram and combination index were utilized to determine this interaction.

Figure 9:
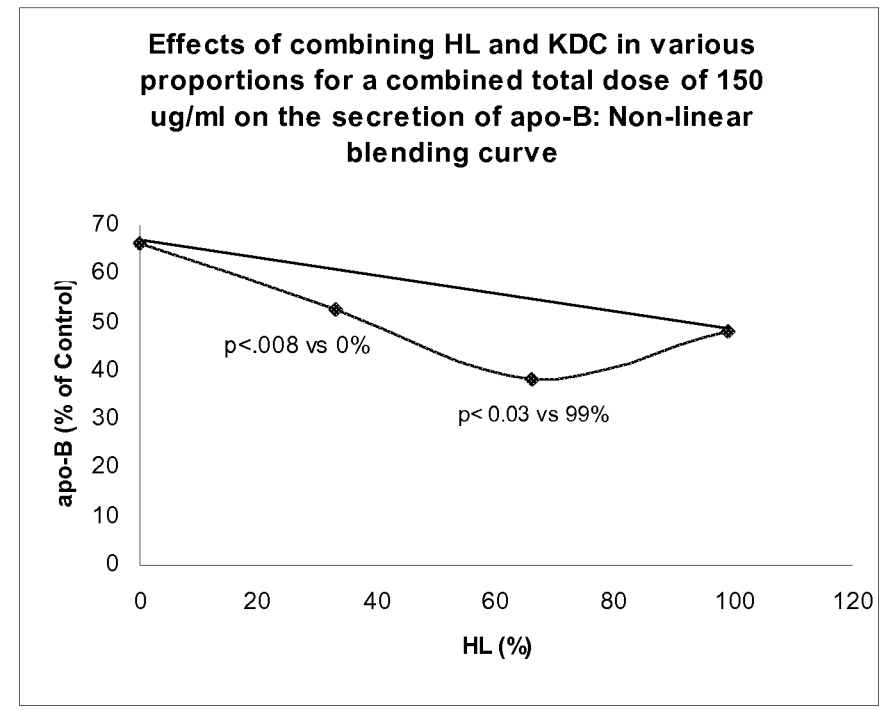
FIG. 9 is a non-linear blending curve plotting how combining an ethanol extract of HL and an ethyl acetate extract of KDC in various proportions for a combined total dose of 150 ug/ml affects the secretion of apolipoprotein-B containing lipoproteins (apo-B) from HepG2 cells.
Figure 10:
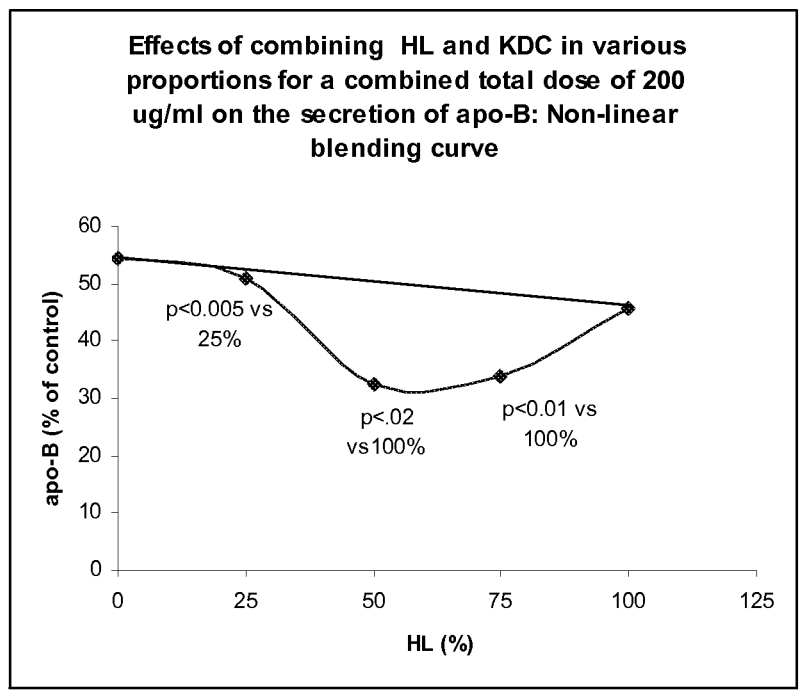
FIG. 10 is a non-linear blending curve plotting how combining an ethanol extract of HL and an ethyl acetate extract of KDC in various proportions for a combined total dose of 200 ug/ml affects the secretion of apolipoprotein-B containing lipoproteins (apo-B) from HepG2 cells.
Figure 11:
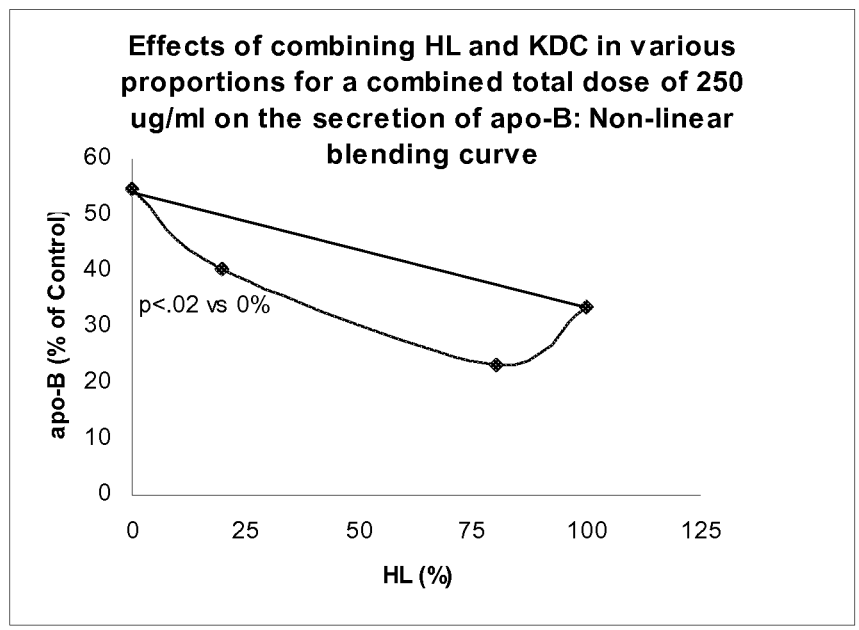
FIG. 11 is a non-linear blending curve plotting how combining an ethanol extract of HL and an ethyl acetate extract of KDC in various proportions for a combined total dose of 250 ug/ml affects the secretion of apolipoprotein-B containing lipoproteins (apo-B) from HepG2 cells.

Non-linear blending curves for a mixture of HL and KDC for total doses of 150 µg/ml, 200 µg/ml and 250 µg/ml are illustrated in FIGS. 9, 10 and 11, respectively. At all these concentrations, increasing the proportion of HL in the mixture was found to increase the efficacy of the extracts, which was reflected in the curving of the line inwards, thereby indicating that the nature of interaction between the two extracts was synergistic.

Figure 12:
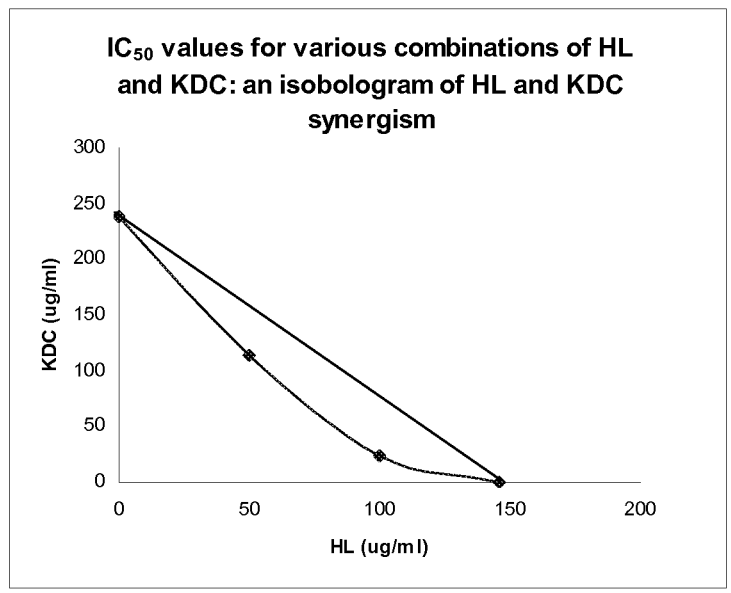
FIG. 12 is an isobologram plotting how combining the ethanol extract of HL and the ethyl acetate extract of Ku Ding Cha (KDC) in various proportions affects the $IC_{50}$ values of the mixture.

Further, the isobologram based on $IC_{50}$ values (Table 1) plotted for various combinations of HL and KDC extracts was found to bend inwards (FIG. 12), further indicating that the nature of interaction between the two extracts was synergistic. FIG. 12 is based on the $IC_{50}$ values of the two extracts (indicating 50% efficacy). It indicates that at HL concentration of 50 ug/ml, 113.2 ug/ml of KDC will be required to achieve 50% inhibition in the secretion of apo-B from HepG2 cells. Whereas when the concentration of HL is increased to 100 ug/ml, then only 23.3 ug of KDC will be required to achieve this effect.

TABLE 1

$IC_{50}$ values of HL and KDC extracts and for various combinations

| Extracts | $IC_{50}$ |
|---|---|
| KDC | 239.1 ug/ml |
| HL | 146.0 ug/ml |
| KDC mixed with 50 ug/ml HL | 163.2 ug/ml |
| KDC mixed with 100 ug/ml HL | 123.3 ug/ml |

The Combination Index

Determination of a drugs combination index (CI) provides quantitative information of the nature of drug interaction. It is calculated through the following equation:

$$CI = (C_{A,x}/IC_{x,A}) + (C_{B,x}/IC_{x,B})$$

$C_{A,x}$ and $C_{B,x}$, are the concentrations of drug A and drug B used in the combination to achieve x% drug effect. $IC_{x,A}$ and $IC_{x,B}$ are the concentrations for single agents to achieve the same effect. A CI of less than, equal to, and more than 1 indicates synergy, additivity, and antagonism, respectively.

For HL 50 µg/ml: 0.81
For HL 100 µg/ml: 0.78

The Combination indexes computed for both the HL concentrations were found to be less than 1. This further indicates that HL and KDC interacted synergistically in reducing the secretion of apo-B from hep-G2 cells.

The combination index was computed from the $IC_{50}$ values and because the $IC_{50}$ value of HL alone was found to be less than 150 ug/ml, combination indexes (CI) for the mixtures containing the amount of HL greater than 150 ug/ml cannot be calculated.

EXAMPLE 4

Figure 13:
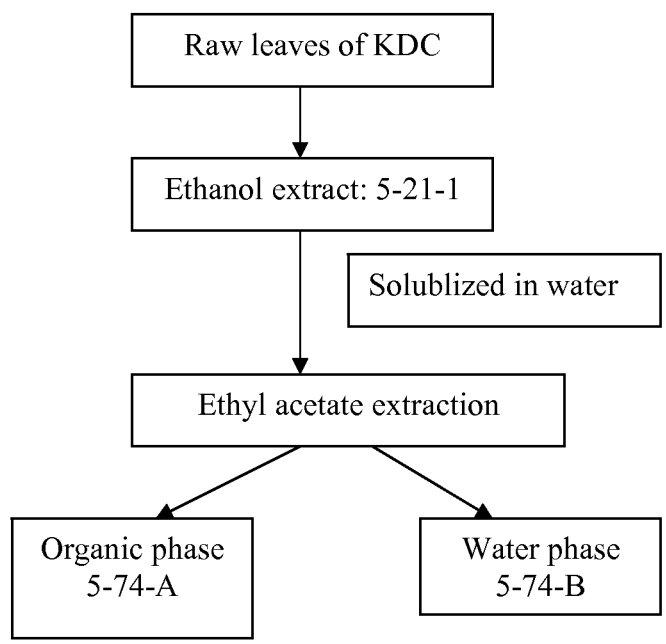
FIG. 13 is a flow diagram illustrating an extraction process for Ku Ding Cha (KDC) leaves.

Determining if the Method of Extraction Affects Observed Biological Activity of KDC To determine if the method of extraction affects the biological activity of KDC, 3 different extracts of KDC were prepared. FIG. 13 indicates the flow diagram revealing the processing techniques utilized in the preparation of these extracts. Raw KDC leaves were initially extracted with ethanol and the extract obtained (5-21-1) was freeze dried and subsequently utilized for the preparation of other extracts and assessment of biological activity. The dried extract (5-21-1) was dissolved in water and further extracted with ethyl acetate. Both organic (5-74-A) and aqueous (5-74-B) phase extracts obtained following ethyl acetate extraction were collected. All extracts obtained from raw leaves during KDC processing were tested for biological activity, both alone as well as in combination, with the ethanol extract of HL.

Figure 14:
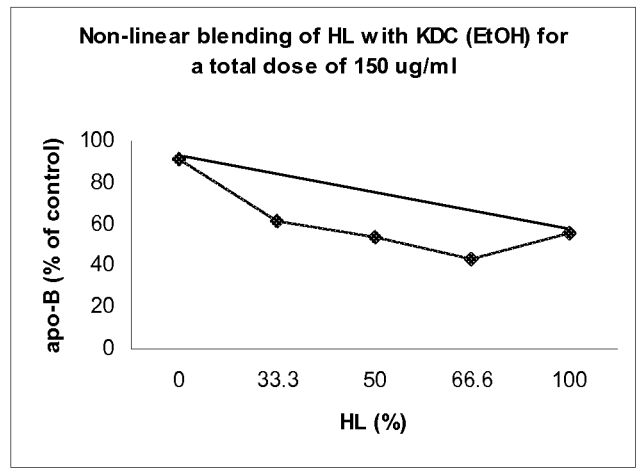
FIG. 14 is a non-linear blending curve plotting how combining an ethanol extract of HL and an ethanol extract of KDC in various proportions for a combined total dose of 150 ug/ml affects the secretion of apolipoprotein-B containing lipoproteins (apo-B) from HepG2 cells.
Figure 15:
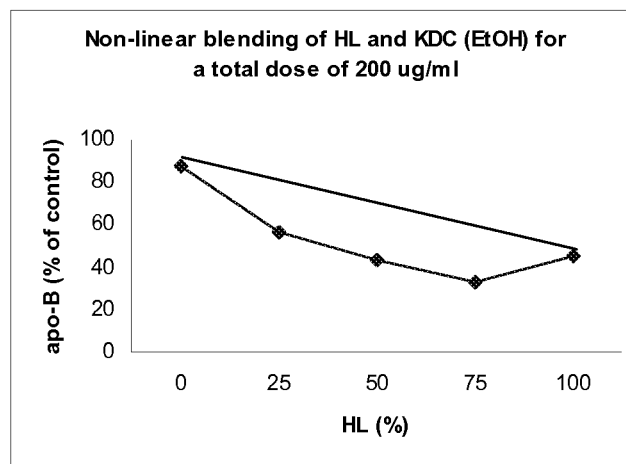
FIG. 15 is a non-linear blending curve plotting how combining an ethanol extract of HL and an ethanol extract of KDC in various proportions for a combined total dose of 200 ug/ml affects the secretion of apolipoprotein-B containing lipoproteins (apo-B) from HepG2 cells.
Figure 16:
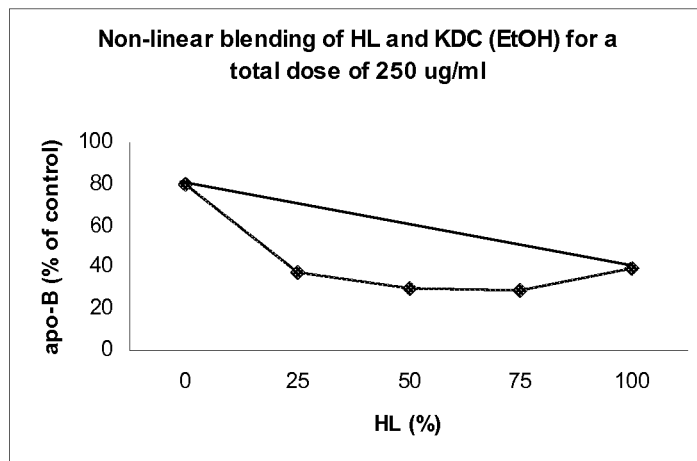
FIG. 16 is a non-linear blending curve plotting how combining an ethanol extract of HL and an ethanol extract of KDC in various proportions for a combined total dose of 250 ug/ml affects the secretion of apolipoprotein-B containing lipoproteins (apo-B) from HepG2 cells.

Interaction between ethanol extracts of KDC and HL: FIGS. 14-16 show the non-linear blending curves between ethanol extract of HL and ethanol extract of KDC (5-21-1) for the combined total doses of 150 ug/ml, 200 ug/ml and 250 ug/ml. Mixtures of these extracts in different proportions were found to have efficacy consistently higher than that of the either of these extracts individually. The results, therefore, indicate synergism between ethanol extracts of HL and KDC in reducing the secretion of apo-B related lipoproteins from hepG2 cells.

Figure 17:
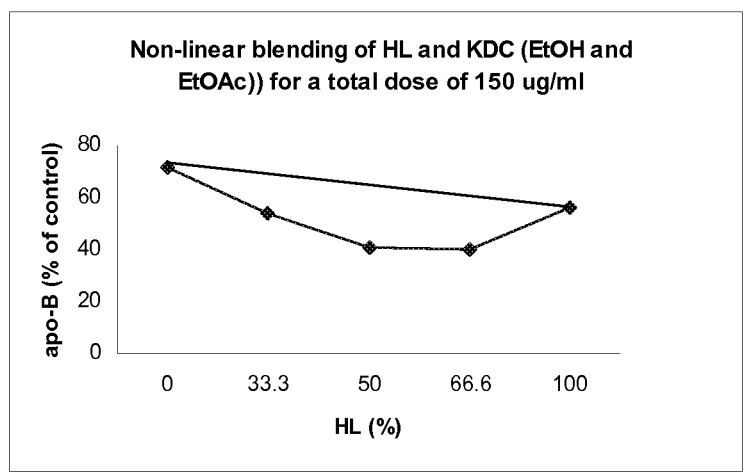
FIG. 17 is a non-linear blending curve plotting how combining an ethanol extract of HL and the organic phase extract of KDC obtained following ethanol and ethyl acetate extractions (5-74-A) in various proportions for a combined total dose of 150 ug/ml affects the secretion of apolipoprotein-B containing lipoproteins (apo-B) from hepG2 cells.
Figure 18:
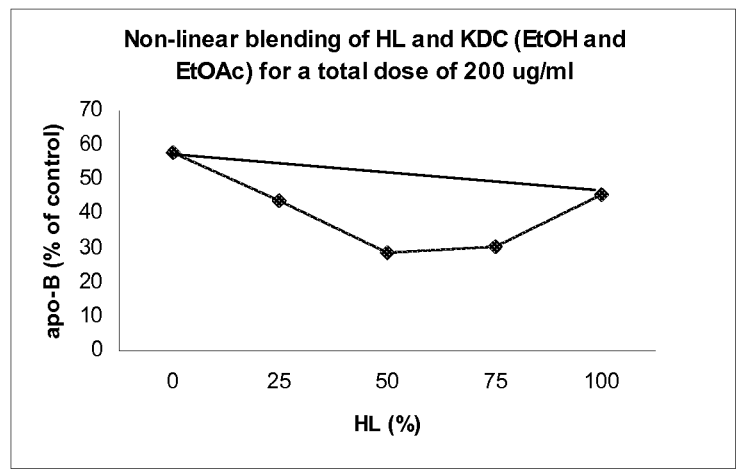
FIG. 18 is a non-linear blending curve plotting how combining an ethanol extract of HL and the organic phase extract of KDC obtained following ethanol and ethyl acetate extractions (5-74-A) in various proportions for a combined total dose of 200 ug/ml affects the secretion of apolipoprotein-B containing lipoproteins (apo-B) from hepG2 cells.

Interaction between the ethyl acetate organic phase extract of KDC (5-74-A) and HL:

FIGS. 17 and 18 illustrate the interaction between the ethanol extract of HL (HL) and the organic phase extract of KDC obtained following both ethanol and then ethyl acetate extractions (5-74-A) for the combined total doses of 150 and 200 ug/ml, respectively. Thus, 5-74-A was found to interact synergistically with the HL extract for both the doses tested in these experiments.

Figure 19:
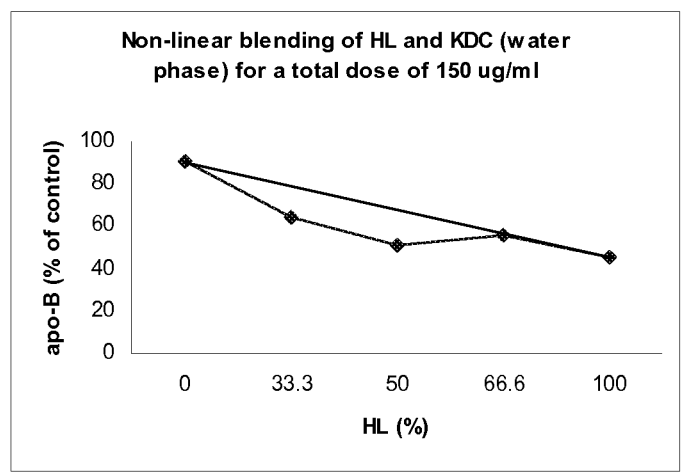
FIG. 19 is a non-linear blending curve plotting how combining an ethanol extract of HL and the water phase extract of KDC obtained following ethanol and ethyl acetate extractions (5-74-B) in various proportions for a combined total dose of 150 ug/ml affects the secretion of apolipoprotein-B containing lipoproteins (apo-B) from hepG2 cells.
Figure 20:
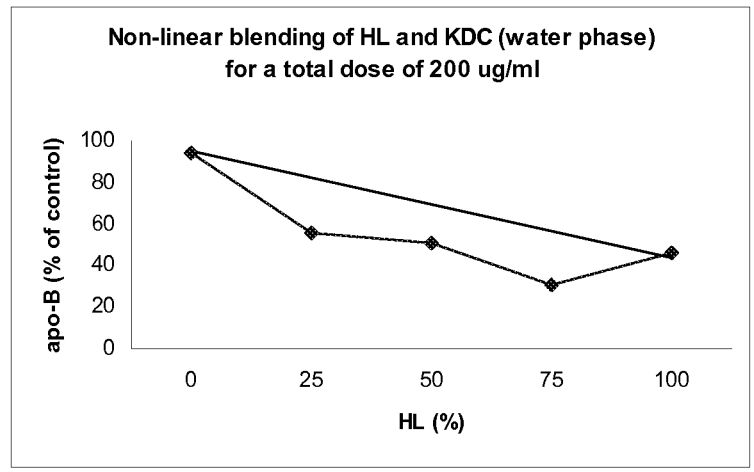
FIG. 20 is a non-linear blending curve plotting how combining an ethanol extract of HL and the water phase extract of KDC obtained following ethanol and ethyl acetate extractions (5-74-B) in various proportions for a combined total dose of 200 ug/ml affects the secretion of apolipoprotein-B containing lipoproteins (apo-B) from hepG2 cells.
Figure 21:
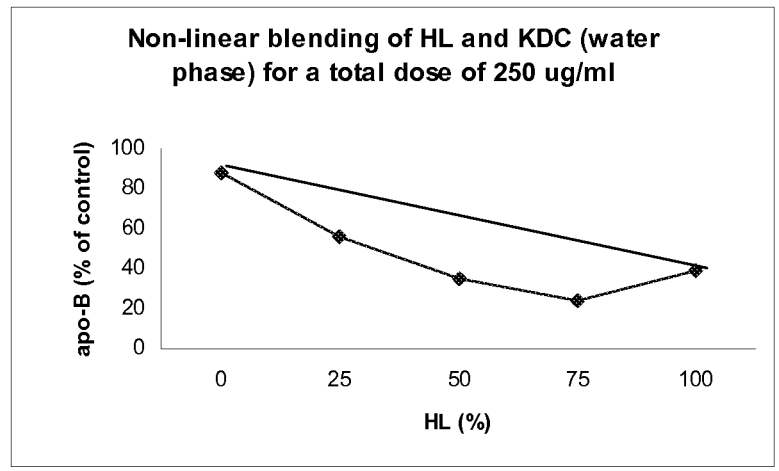
FIG. 21 is a non-linear blending curve plotting how combining an ethanol extract of HL and the water phase extract of KDC obtained following ethanol and ethyl acetate extractions (5-74-B) in various proportions for a combined total dose of 250 ug/ml affects the secretion of apolipoprotein-B containing lipoproteins (apo-B) from hepG2 cells.

Interaction between the water phase extract of KDC (5-74-B) and HL: FIGS. 19, 20, and 21 show the non-linear blending curves for the mixtures containing the ethanol extract of HL and the water phase extract of KDC obtained following both ethanol and then ethyl acetate extractions (5-74-B). FIGS. 19-21 demonstrate that HL interacts synergistically with the 5-74-B extract of KDC.

Figure 22:
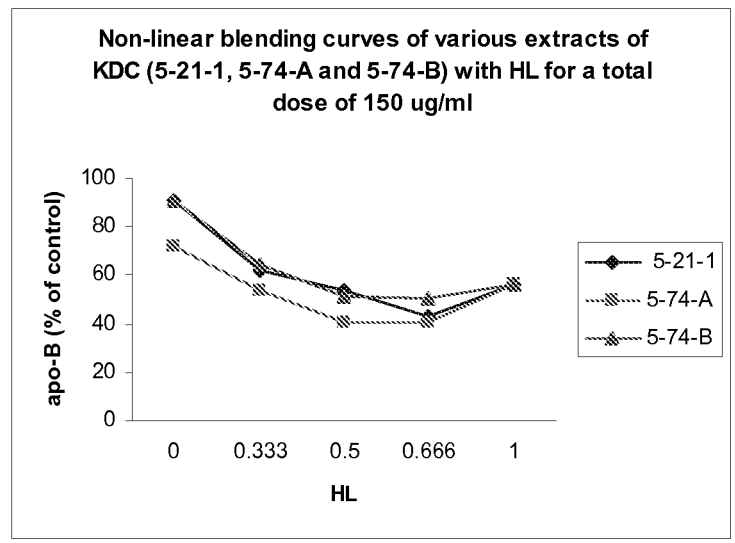
FIG. 22 is a non-linear blending curve plotting how combining each of 3 different extracts of Ku Ding Cha (KDC) with ethanol extracts of HL in various proportions for a combined total dose of 150 ug/ml affects the secretion of apolipoprotein-B containing lipoproteins (apo-B) from hepG2 cells. 5-21-1 is the ethanol extract of KDC; 5-74-A is the organic phase extract obtained following ethanol and ethyl acetate extraction of KDC; and 5-74-B is the water phase extract obtained following ethanol and ethyl acetate extraction of KDC.
Figure 23:
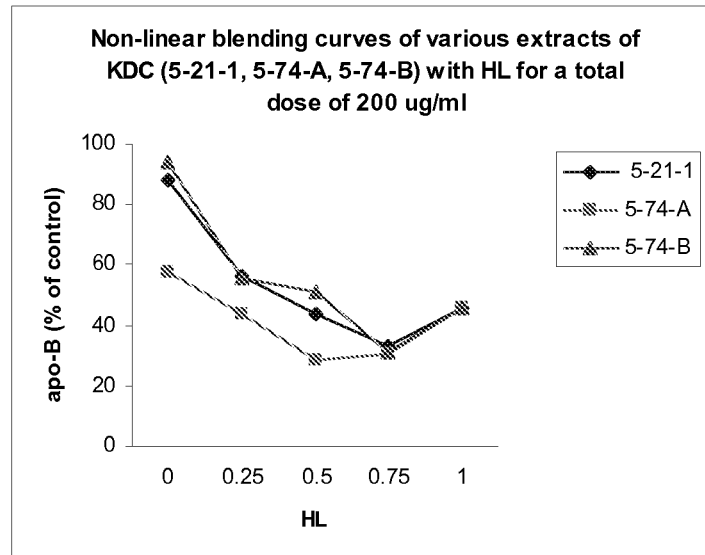
FIG. 23 is a non-linear blending curve plotting how combining each of 3 different extracts of Ku Ding Cha (KDC) with ethanol extracts of HL in various proportions for a combined total dose of 200 ug/ml affects the secretion of apolipoprotein-B containing lipoproteins (apo-B) from hepG2 cells. 5-21-1 is the ethanol extract of KDC; 5-74-A is the organic phase extract obtained following ethanol and ethyl acetate extraction of KDC; and 5-74-B is the water phase extract obtained following ethanol and ethyl acetate extraction of KDC.
Figure 24:
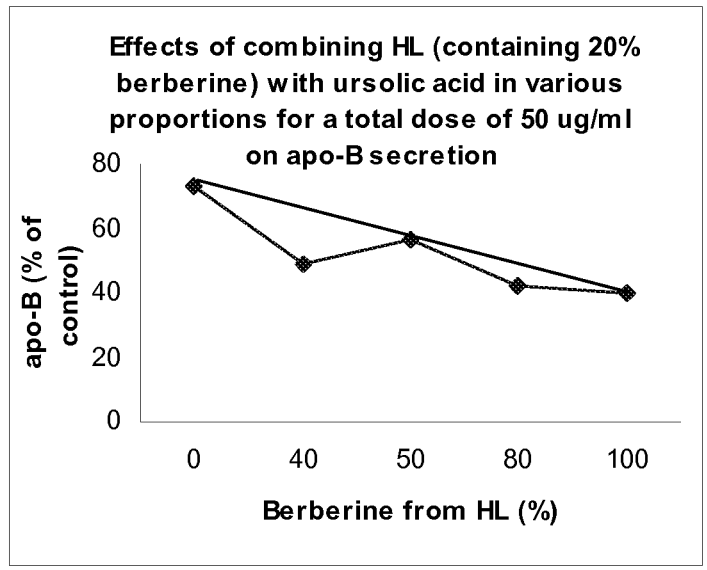
FIG. 24 is a non-linear blending curve plotting how combining an ethanol extract of HL with ursolic acid in various proportions for a combined total dose of 50 ug/ml affects the secretion of apolipoprotein-B containing lipoproteins (apo-B) from hepG2 cells.
Figure 25:
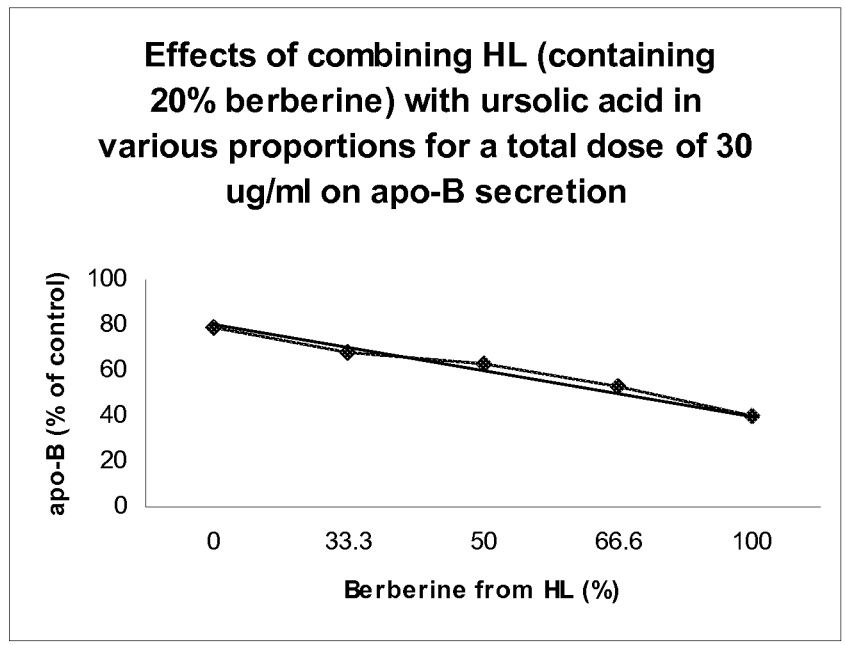
FIG. 25 is a non-linear blending curve plotting how combining an ethanol extract of HL with ursolic acid in various proportions for a combined total dose of 30 ug/ml affects the secretion of apolipoprotein-B containing lipoproteins (apo-B) from hepG2 cells.
Figure 26:
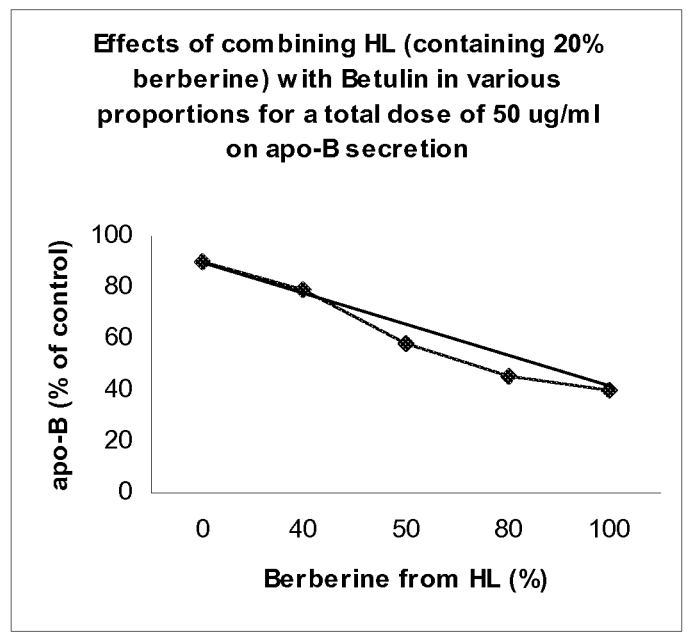
FIG. 26 is a non-linear blending curve plotting how combining an ethanol extract of HL with betulin in various proportions for a combined total dose of 50 ug/ml affects the secretion of apolipoprotein-B containing lipoproteins (apo-B) from hepG2 cells.
Figure 27:
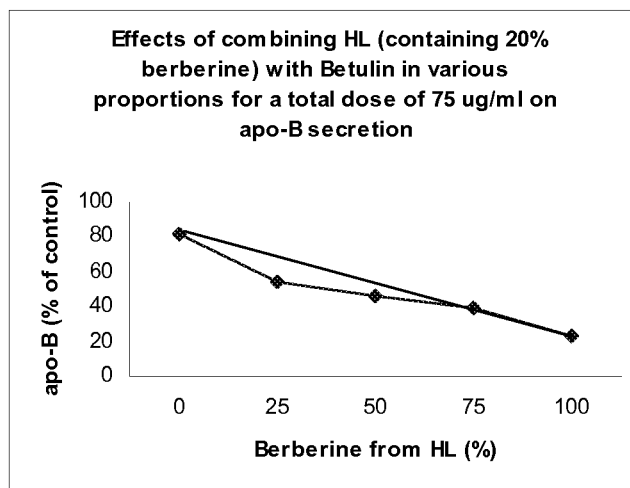
FIG. 27 is a non-linear blending curve plotting how combining an ethanol extract of HL with betulin in various proportions for a combined total dose of 75 ug/ml affects the secretion of apolipoprotein-B containing lipoproteins (apo-B) from hepG2 cells.
Figure 28:
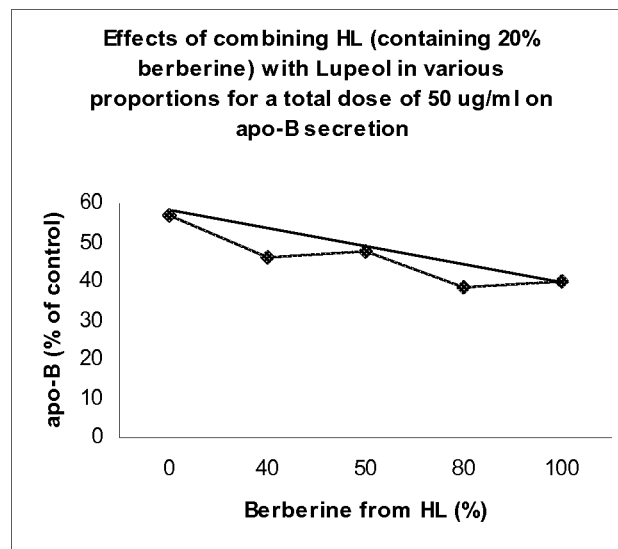
FIG. 28 is a non-linear blending curve plotting how combining an ethanol extract of HL with lupeol in various proportions for a combined total dose of 50 ug/ml affects the secretion of apolipoprotein-B containing lipoproteins (apo-B) from hepG2 cell.
Figure 29:
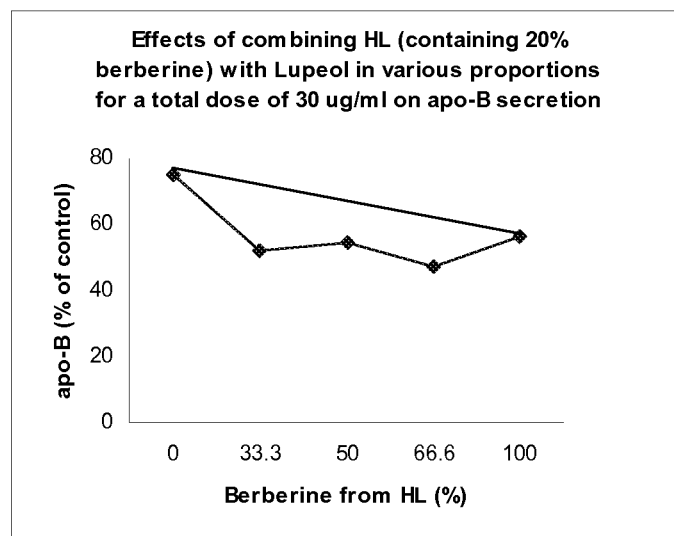
FIG. 29 is a non-linear blending curve plotting how combining an ethanol extract of HL with lupeol in various proportions for a combined total dose of 30 ug/ml affects the secretion of apolipoprotein-B containing lipoproteins (apo-B) from hepG2 cells.

As demonstrated in FIGS. 14 to 21, the method of extraction for KDC does not affect its synergistic interaction with HL. Among the three extracts, 5-74-A was found to have the greatest synergism with HL (FIGS. 22 and 23).

EXAMPLE 5

Interaction Between Triterpenoids, Ursolic Acid, Betulin, and Lupeol, and HL

Chemical analysis of 5-74-A revealed that it contained various triterpenoids and, in particular, significant amounts of lupeol, betulin and ursolic acid were found in this extract. The next sets of experiments, therefore, were designed to determine the nature of interaction between each of these triterpenoids and the ethanol extract of HL.

The experiments described in FIGS. 24-29 were based on the prior laboratory analysis indicating that HL contains about 20% BBR. Therefore, a value of 20% of BBR in HL was combined with either ursolic acid or lupeol to prepare a mixture of combined total doses of 30 or 50 ug/ml. For example in FIG. 24, for a total dose of 50 ug/ml with 40% BBR content, 20 ug/ml of BBR is required; thus, 100 ug/ml of HL was added to 30 ug/ml of ursolic acid (for 60% ursolic acid content). In a similar fashion, 20% of BBR in HL was combined with betulin to prepare a mixture of combined total doses of 50 and 75 ug/ml. The non-linear blending curves of each of these terpenoids with HL are shown in FIGS. 24-29. It appears, therefore, that triperpenoids, in particular ursolic acid, betulin and lupeol, are likely a few of the constituents of KDC interacting with HL.

EXAMPLE 6

Interactions Between KDC Aqueous Sub-Fractions, 94-1, 94-2, 94-3, and Huanglian

Subsequent to completion of above described experiments, 5-74-B, the water phase extract that was obtained following the ethanol and ethyl acetate extraction of KDC, was further fractionated by water elution through a Sephadex-15 column and 3 fractions were successively collected and named fractions 94-1, 94-2 and 94-3.

Figure 30:
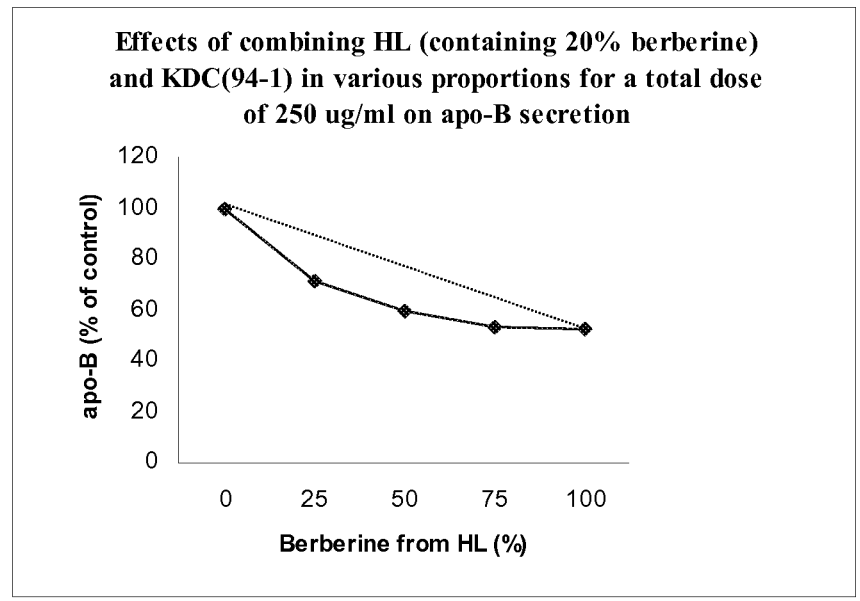
FIG. 30 is a non-linear blending curve plotting how combining an ethanol extract of HL and a sub-fraction of a water phase extract of KDC (94-1), in various proportions for a combined total dose of 250 ug/ml affects the secretion of apolipoprotein-B containing lipoproteins (apo-B) from hepG2 cells.

Interaction between 94-1 and ethanol extract of HL: FIG. 30 depicts the non-linear blending curve for various mixtures of 94-1 and the HL extract. As is evident from FIG. 30, 94-1 interacted synergistically with HL.

Figure 31:
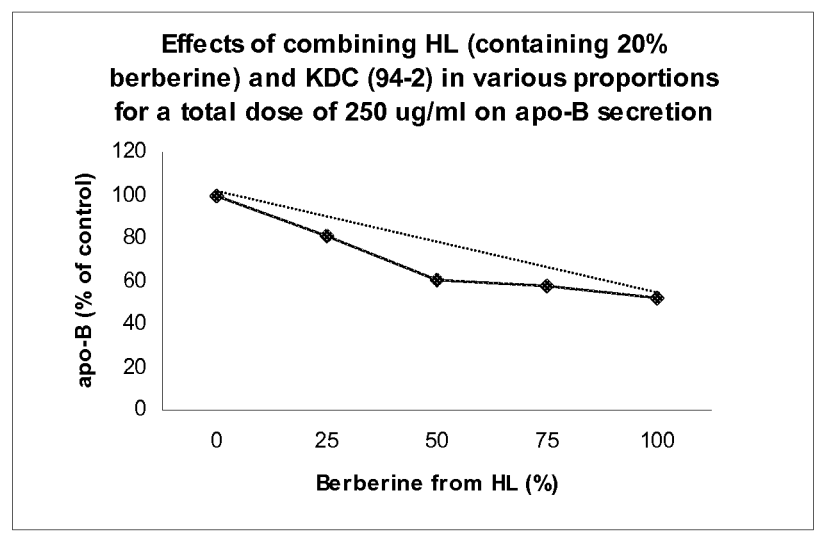
FIG. 31 is a non-linear blending curve plotting how combining the ethanol extract of HL and a sub-fraction of water phase extract of KDC (94-2), in various proportions for a combined total dose of 250 ug/ml, affects the secretion of apolipoprotein-B containing lipoproteins (apo-B) from hepG2 cells.

Interaction between 94-2 and ethanol extract of HL: FIG. 31 demonstrates that 94-2 is also synergistic when combined with HL.

Figure 32:
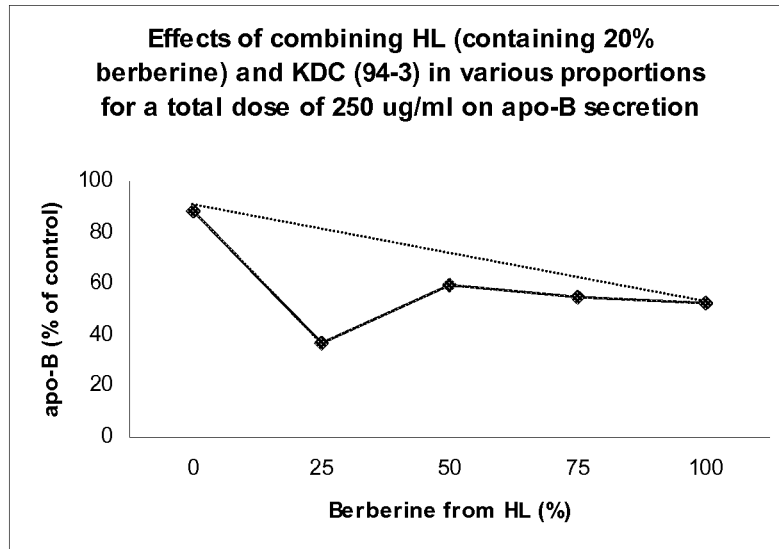
FIG. 32 is a non-linear blending curve plotting how combining the ethanol extract of HL and a subfraction of water phase extract of KDC (94-3), in various proportions for a combined total dose of 250 ug/ml, affects the secretion of apolipoprotein-B containing lipoproteins (apo-B) from hepG2 cells.

Interaction between 94-3 and the ethanol extract of HL: FIG. 32 demonstrates that 94-3 is also synergistic when combined with HL. The effects are most apparent in a 94-3 to HL weight of 3:1.

Figure 33:
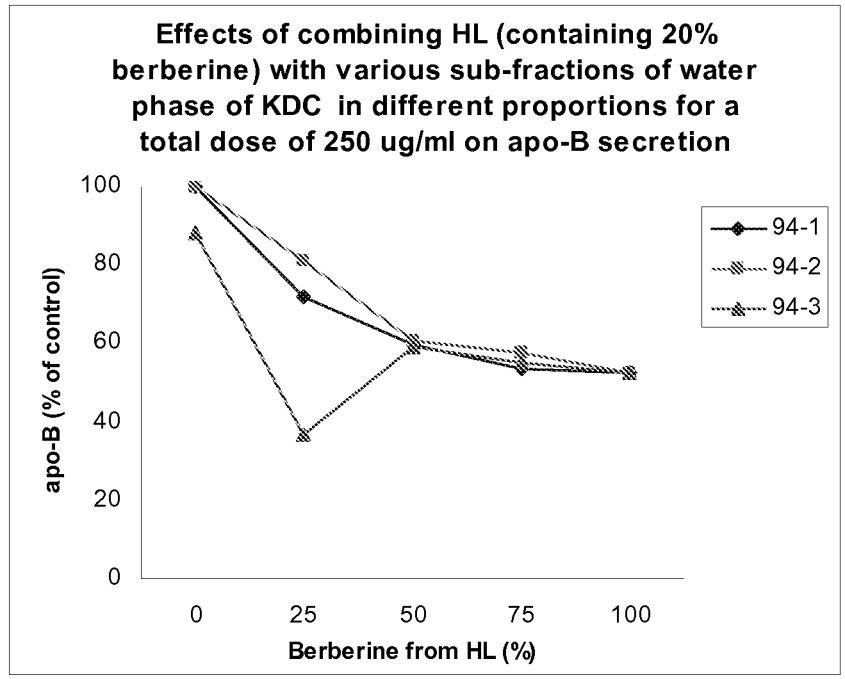
FIG. 33 is a non-linear blending curve plotting how combining each of 3 different sub-fractions of water phase extracts of KDC with an ethanol extract of HL in various proportions for a combined total dose of 250 ug/ml affects the secretion of apolipoprotein-B containing lipoproteins (apo-B) from hepG2 cells. 94-1 is the first sub-fraction of 5-74-B; 94-2 is the second sub-fraction of 5-74-B: 94-3 is the third sub-fraction of 5-74-B.

As demonstrated in FIGS. 30 to 32, each sub-fraction of 5-74-B are synergistic with HL. Among the 3 sub-fractions of the water phase extract 5-74-B, 94-3 has the greatest synergy with HL (see FIG. 33).

EXAMPLE 7

Chemical analysis of 94-3 revealed that the one of the major constituents of this fraction was a caffeoyl quinic acid called chlorogenic acid. Subsequent experiments, therefore, were designed to determine the nature of interaction between chlorogenic acid and the ethanol extract of HL.

Figure 34:
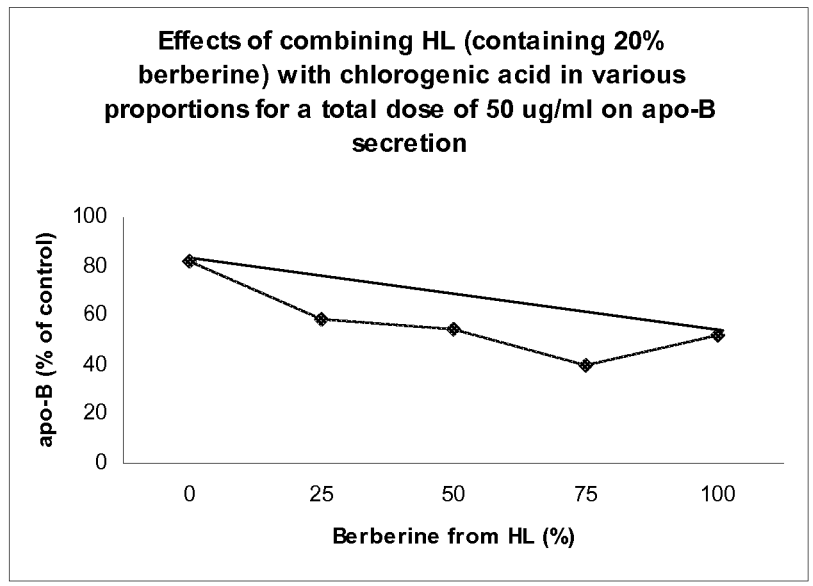
FIG. 34 is a non-linear blending curve plotting how combining an ethanol extract of HL with chlorogenic acid in various proportions for a combined total dose of 50 ug/ml affects the secretion of apolipoprotein-B containing lipoproteins (apo-B) from hepG2 cells.
Figure 35:
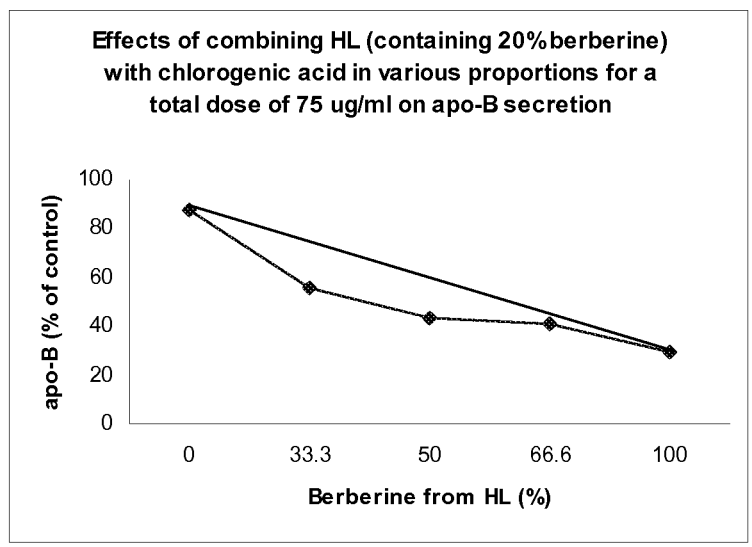
FIG. 35 is a non-linear blending curve plotting how combining an ethanol extract of HL with chlorogenic acid in various proportions for a combined total dose of 75 ug/ml affects the secretion of apolipoprotein-B containing lipoproteins (apo-B) from hepG2 cells.
Figure 36:
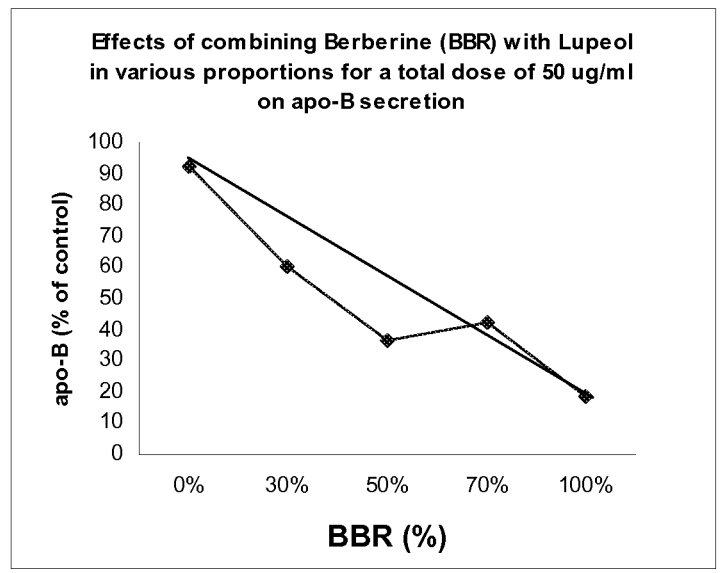
FIG. 36 is a non-linear blending curve plotting how combining berberine (BBR) with lupeol in various proportions for a combined total dose of 50 ug/ml affects the secretion of apolipoprotein-B containing lipoproteins (apo-B) from hepG2 cells.
Figure 37:
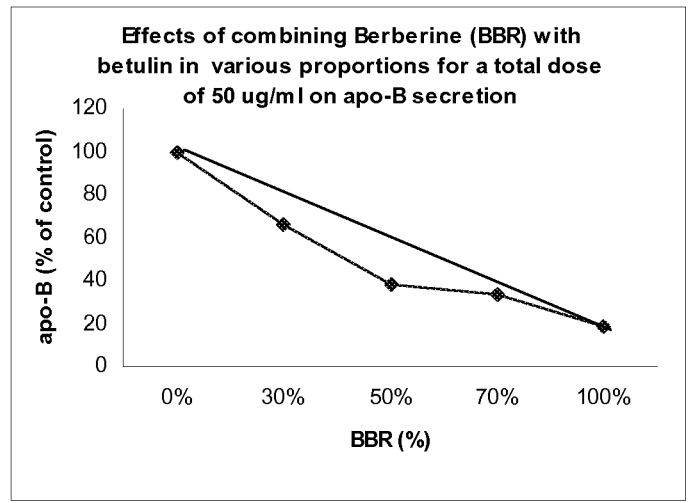
FIG. 37 is a non-linear blending curve plotting how combining berberine (BBR) with betulin in various proportions for a combined total dose of 50 ug/ml affects the secretion of apolipoprotein-B containing lipoproteins (apo-B) from hepG2 cells.
Figure 38:
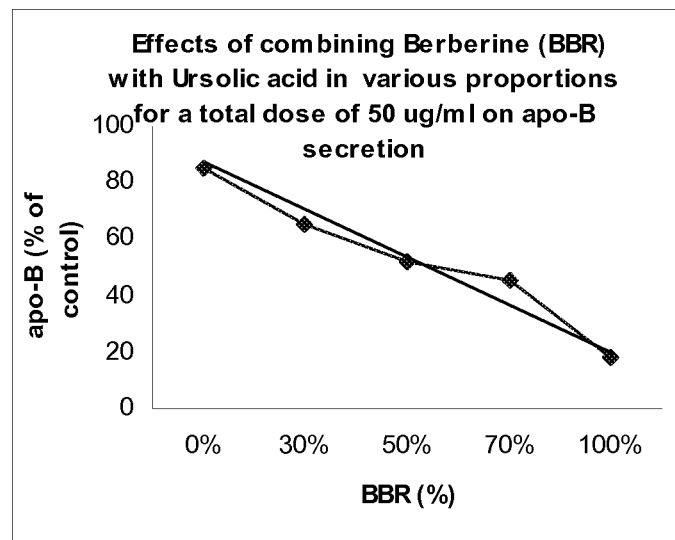
FIG. 38 is a non-linear blending curve plotting how combining berberine (BBR) with ursolic acid in various proportions for a combined total dose of 50 ug/ml affects the secretion of apolipoprotein-B containing lipoproteins (apo-B) from hepG2 cells.
Figure 39:
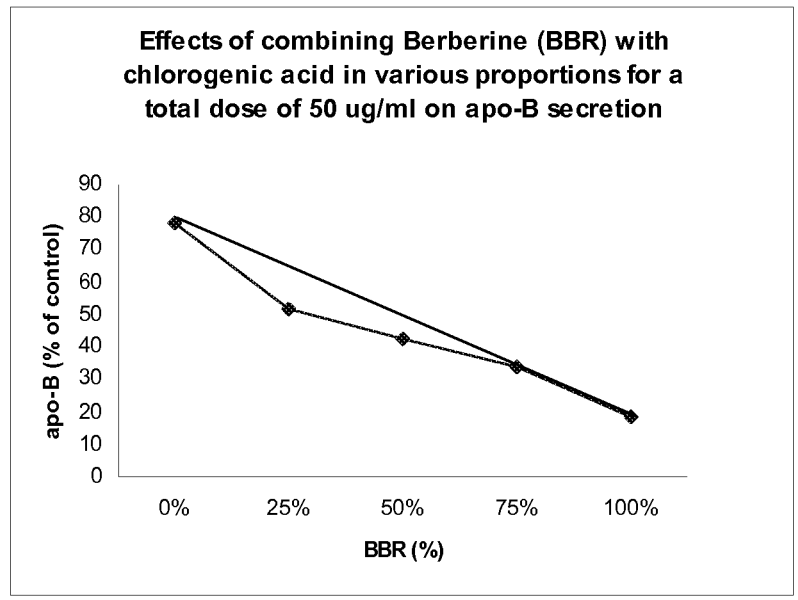
FIG. 39 is a non-linear blending curve plotting how combining berberine (BBR) with chlorogenic acid in various proportions for a combined total dose of 50 ug/ml affects the secretion of apolipoprotein-B containing lipoproteins (apo-B) from hepG2 cells.

Interaction between chlorogenic acid and the ethanol extract of HL: Chlorogenic acid and the ethanol extract of HL were mixed together in various proportions to study its interactions. The effects of these combinations are illustrated at the combined total dose of 50 and 75 ug/ml in FIGS. 34 and 35. Chlorogenic acid also expressed synergism with the HL extract, indicating that the chlorogenic acid content of the KDC extracts is likely contributing to the demonstrated synergism between HL and KDC.

EXAMPLE 8

Experiments were devised to consider the synergism between BBR and various potential active components of KDC (pure compounds including lupeol, betulin, ursolic acid, and chlorogenic acid). The following graphs illustrate the synergism between BBR and these pure compounds in FIGS. 36-39.

EXAMPLE 9

Figure 40:
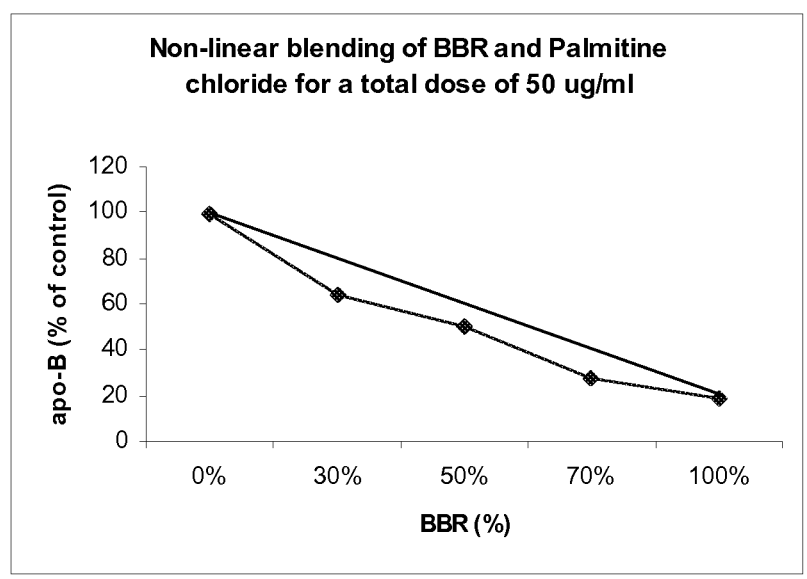
FIG. 40 is a non-linear blending curve plotting how combining berberine (BBR) with palmitine chloride in various proportions for a combined total dose of 50 ug/ml affects the secretion of apolipoprotein-B containing lipoproteins (apo-B) from hepG2 cells.

An experiment was also carried out to determine the nature of interaction between different components of HL. Therefore, the nature of interaction between berberine and palmitine chloride was determined and is presented in FIG. 40. Palmitine chloride was also found to interact synergistically with berberine.

Full Citations for References Referred to in the Specification

1. Raza J A, Babb J D, Movaheed A. 2004. Optimal management of hyperlipidemia in primary prevention of cardiovascular disease. Int. J. Cardiol. 97: 355-366.
2. Arad Y, Ramakrishnan R, Ginsberg H N. 1992. Effects of lovastatin therapy on very-low-density lipoprotein triglyceride metabolism in subjects with combined hyperlipidemia: evidence for reduced assembly and secretion of triglyceride-rich lipoproteins. Meatbolism. 41: 487-493.
3. Reihner E, Rudling M, Stahlberg D, Berglund L, Ewerth S, Bjorkhem I. et al. 1990. Influence of pravastatin, a specific inhibitor of HMG-CoA reductase, on hepatic metabolism of cholesterol. N. Engl. J. Med. 323: 224-228.
4. Bays H. 2006. Statin safety: an overview and assessment of the data-2005. Am. J. Cardiol. 97(8A): 6C-26C.
5. Hamilton-Craig I. 2001. Statin associated myopathy. Med. J. Aust. 175(9): 486-489.
6. Kong W, Wei J, Abidi P, Lin M, Inaba S, Li C. et al., 2004. Berberine is a novel cholesterol-lowering drug working through a unique mechanism distinct from statins. Nature Med. 10: 1344-1351.

7. Abidi P, Chen W, Kraemer F B, Li H, Liu J. 2006. The medicinal plant goldenseal is a natural LDL-cholesterol agent with multiple bioactive components and new action of mechanisms. J. Lipid Res. 47: 2134-2147.
8. Brusq J, Ancellin N, Grondin P, Guillard R, martin S, Saintillan Y. et al. 2006. Inhibition of lipid synthesis through activation of AMP-kinase: an additional mechanism for the hypolipidemic effects of berberine. J. Lipid Res. 47: 1274-1280.
9. Huang C, Zhang Y, Gong Z, Sheng X, Li Z, Zhang W. et al. 2006. Berberine inhibits 3T3-L1 adipocyte differentiation through the PPAR γ pathway. Biochem. Biophys. Res. Comm. 348: 571-578.
10. Anis K V, Kuttan G, Kuttan R. 1999. Role of berberine as an adjuvant response modifier during tumor therapy in mice. Phar. Pharmacol. Comm. 5: 697-700.
11. Etheridge A S, Black S R, Patel P R, So J, Mathews J M. 2007. An in vitro evaluation of cytochrome P450 inhibition and P-glycoprotein interaction with goldenseal, *Ginkgo biloba*, grape seed, milk thistle, and ginseng extracts and their constituents. Planta Med. 73: 731-741.
12. Negishi O, Negishi Y, Yamaguchi F, Sugahara T. 2004. Deodorization with Ku-ding-cha containing a large amount of caffeoyl quinic acid derivatives. J. Agric. Food Chem. 52: 5513-5518.
13. Lau K, He Z, Dong H, Fung K, But P P. 2002. Antioxidative, anti-inflammatory and hepato-protective effects of *Ligustrum robustum*. J. Ethnopharmacol. 83: 63-71.
14. Gugliucci A. 1996. Antioxidant effects of *Ilex paraguariensis*: Induction of decreased oxidability of human LDL in vivo. Biochem. Biophys. Res. Comm. 224: 338-344.
15. Gugliucci A, Stahl A J. 1995. Low-density lipoprotein oxidation is inhibited by extracts of Ilex Paraguariensis. Biochem. Mol. Bio. Iterations. 35: 47-56.
16. Stein F L P, Schmidt B, Furlong E B, Soares L A S, Soares M C F, Vaz M R C, Baisch A L M. 2005. Vascular responses to extractable fractions of *Ilex paraguariensis* in rats fed standard and high-cholesterol diets. Biol. Res. Nurs. 7: 146-156.
17. Wang S S, Chen J H, Liu X J. 1994. Preliminary study on pharmacologic action of *Ligustrum japonicum*. Zhongguo Zhong Xi Yi Jie He Za Zhi. 14: 670-972 (article in Chinese).
18. Tang L, Jiang Y, Chang H, Zhao M, Tu P, Cui J et al. 2005. Triterpene saponins from the leaves of *Ilex Kudincha*. J. Nat. Prod. 68: 1169-1174.
19. Ouyang M, Yang C, Wu Z. 2001. Triterpenoid saponins from the leaves of *Ilex Kudincha*. J. Asian Nat. Products Res. 3: 31-42.
20. Staudt M, Mandl N, Joffre r, rambal S. 2001. Intraspecific variability of monoterpene composition emitted by *Quercus ilex* leaves. Can. J. For. Res. 31: 174-180.
21. Jun T, Zhang H, Sun H, Pan L, Pin Y, Chen D. 1998. Monoterpenoid glycosides from *Ligustrum robustum*. Phytochemistry 48: 1013-1018.
22. Ouyang M, Wang H, Chen Z, Yang C. 1996. Triterpenoid glycosides from *Ilex Kudincha*. Phytochemistry. 43: 443-445.
23. He Z, Ueda S, Akaji M, Fujita T, Inoue K, Yang C. 1994. Monoterpenoid and phenylethanoid from *Ligustrum pedunculare*. Phytochemistry. 36: 709-716.
24. Im K, Jeong T, Kwon B, Baek N, Kim s, Kim D K. 2006. Acyl-CoA: Cholesterol Acyltransferase inhibitors from *Ilex macropoda*. Arch. Pharm. Res. 29; 191-194.
25. Nishimura K, Fukuda K, Miyase t, Noguchi H, Chen X. 1999. Activity-guided isolation of triterpenoid Acyl Coa Cholesteryl Acyl Transferase (ACAT) inhibitors from *Ilex kudincha*. J. Nat. Prod. 62: 1061-1064.
26. Nishimura K, Miyase T, Noguchi H. 1999b. Triterpenoid saponins from *Ilex kudincha*. J. nat. Prod. 62: 1128-1133.
27. Fukuda T, Kitada Y, Chen X M, Yang L, Miyase t. 1996. Two new monoterpene glycosides from ku-ding-cha. Inhibitors of acyl-CoA: cholesterol acyltransferase (ACAT). Chem. Phar. Bull. 44: 2173-2176.
28. Leon C, Hill J S, Wasan K M. 2005. Potential role of acyl-coenzyme A: cholesterol transferase (ACAT) inhibitors as hypolipidemic and antiatherosclerosis drugs. Pharm. Res. 10: 1578-1588.
29. Zollner 1999 handbook of enzyme inhibitors, Wiley-VCH, Weinheim, Germany.
30. Asai T, Takeuchi T, Diffenderfer J, Sibley L D. 2002. Identification of small-molecule inhibitors of nucleoside triphosphate hydrolase in *Toxoplasma gondii*. Antimicrob Agents Chemother. 46: 2393-9.
31. Lee W S, Im K R, Park Y D, Sung N D, Jeong T S. 2006. Human ACAT-1 and ACAT-2 inhibitory activities of pentacyclic triterpenes from the leaves of *Lycopus lucidus* TURCZ. Biol Pharm Bull. 29(2):382-4.
32. Novotny L, Vachalkova A, Biggs D. 2001. Ursolic acid: an anti-tumorigenic and chemopreventive activity. Minireview. Neoplasma. 48(4):241-6.
33. Patocka, J. 2003. Biologically active pentacyclic triterpenes and their current medicine signification. J. Appl. Biomed. 1: 7-12.
34. Chung M Y, Rho M C, Lee S W, Park H R, Kim K, Lee I A, Kim D H, Jeune K H, Lee H S, Kim Y K. 2006. Inhibition of diacylglycerol acyltransferase by betulinic acid from *Alnus hirsuta*. Planta Med. 72(3): 267-9.
35. Lee T K, Poon R T, Wo J Y, Ma S, Guan X Y, Myers J N, Altevogt P, Yuen A P. 2007. Lupeol suppresses cisplatin-induced nuclear factor-kappaB activation in head and neck squamous cell carcinoma and inhibits local invasion and nodal metastasis in an orthotopic nude mouse model. Cancer Res. 67(18):8800-9.
36. Choi S W, Hur N Y, Ahn S C, Kim D S, Lee J K, Kim D O, Park S K, Kim B Y, Baik M Y. 2007. Isolation and structural determination of squalene synthase inhibitor from *Prunus mume* fruit. J Microbiol Biotechnol. 17(12):1970-5.
37. Rajendran S, Deepalakshmi P D, Parasakthy K, Devaraj H, Devaraj S N. 1996. Effect of tincture of *Crataegus* on the LDL-receptor activity of hepatic plasma membrane of rats fed an atherogenic diet. Atherosclerosis. 123:235-41.
38. Thrift R N, Forte T M, Cahoon B E, Shore V G. 1986 Characterization of lipoproteins produced by the human liver cell line, Hep G2, under defined conditions. J. Lipid Res. 27: 236-241.
39. Sorci-Thomas M, Hendricks C L, Kearns M W. 1992. HepG2 cell LDL receptor activity and the accumulation of apolipoprotein B and E in response to docosahexaenoic acid and cholesterol. J. Lipid Res. 33: 1147-1156.
40. Wu G Y, Wu Ch, Rifici V A, Stockert R J. 1984. Activity and regulation of low density lipoprotein receptors in a human hepatoblastoma cell line. Hepatology 4(6): 1190-1194.

The invention claimed is:
1. A synergistic blood lipid lowering composition comprising synergistically effective amounts of HL and KDC, wherein the weight ratio of HL to KDC is between about 25% and 75%, wherein the HL is a Huanglian extract obtained by a method comprising extraction of *Coptis chinensis* with water or ethanol, and wherein the KDC is a Ku Ding Cha extract obtained by a method comprising extraction of *Ilex kudingcha* with water, ethanol or ethyl acetate.

2. The composition of claim 1, further comprising an effective amount of a hawthorn extract.

3. The composition of claim 1, wherein the weight ratio of HL to KDC is between 33% and 67%.

4. The composition of claim 3, wherein the weight ratio of HL to KDC is between 40% and 60%.

5. The composition of claim 4, wherein the weight ratio of HL to KDC is about 1:1.

6. The composition of claim 1, wherein the composition further comprises a carrier which is a food or beverage.

7. The composition of claim 1 in combination with another medicament or with one or more pharmaceutical acceptable carriers for the lowering of blood lipid levels.

8. The composition of claim 7, wherein the carrier is a food or a beverage.

9. A method of lowering the blood lipid levels in a patient in need of such lowering, comprising administering to the patient an effective amount of the composition according to claim 1.

10. The method of claim 9, wherein the composition is administered orally.

11. The method of claim 9, wherein the composition is orally administered to the patient in a food or beverage.

12. The method of claim 9, wherein the blood lipid levels that are lowered comprise triglyceride levels.

13. The method of claim 9, wherein the blood lipid levels that are lowered comprise low-density-lipoprotein cholesterol levels.

14. The method of claim 9, wherein the blood lipid levels that are lowered comprise total cholesterol levels.

15. The method of claim 9, wherein the mammal is a human.

16. The composition of claim 1, wherein the HL is from *Coptis chinensis* Franch.

17. The composition of claim 1, wherein the KDC is from *Ilex kudingcha* C. J. Tseng (*Aquifoliaceae*).

18. The composition of claim 1, wherein the blood lipids are triglycerides, low-density-lipoprotein cholesterol or total cholesterol.

19. The composition of claim 1, wherein the method for obtaining the Ku Ding Cha extract comprises extraction of *Ilex kudingcha* with ethanol to obtain a first extract, drying the first extract to obtain a dried extract, dissolving the dried extract in water to provide a resuspended extract, extracting the resuspended extract with ethyl acetate and separating the ethyl acetate phase to provide the Ku Ding Cha extract.

20. The composition of claim 1, wherein the method for obtaining the Ku Ding Cha extract comprises extraction of *Ilex kudingcha* with ethanol to obtain a first extract, drying the first extract to obtain a dried extract, dissolving the dried extract in water to provide a resuspended extract, extracting the resuspended extract with ethyl acetate and separating the aqueous phase to provide the Ku Ding Cha extract.

21. The composition of claim 1, wherein the Huanglian extract is obtained by a method comprising extraction of *Coptis chinensis* with water and the Ku Ding Cha extract is obtained by a method comprising extraction of *Ilex kudingcha* with water.

22. The composition of claim 1, wherein the HL extract is obtained by a method comprising extraction of *Coptis chinensis* with ethanol and the Ku Ding Cha extract is obtained by a method comprising extraction of *Ilex kudingcha* with ethanol.

23. The composition of claim 1, wherein the Huanglian extract is obtained by a method comprising extraction of *Coptis chinensis* with ethanol and the Ku Ding Cha extract is obtained by a method comprising extraction of *Ilex kudingcha* with ethyl acetate.

24. The composition of claim 1, wherein the Huanglian extract is obtained by a method comprising extraction of *Coptis chinensis* with ethanol, and wherein the Ku Ding Cha extract is obtained by a method comprising extraction of *Ilex kudingcha* with ethanol to obtain a first extract, drying the first extract to obtain a dried extract, dissolving the dried extract in water to provide a resuspended extract, extracting the resuspended extract with ethyl acetate and separating the ethyl acetate phase to provide the Ku Ding Cha extract.

25. The composition of claim 1, wherein the Huanglian extract is obtained by a method comprising extraction of *Coptis chinensis* with ethanol, and wherein the Ku Ding Cha extract is obtained by a method comprising extraction of *Ilex kudingcha* with ethanol to obtain a first extract, drying the first extract to obtain a dried extract, dissolving the dried extract in water to provide a resuspended extract, extracting the resuspended extract with ethyl acetate and separating the aqueous phase to provide the Ku Ding Cha extract.

* * * * *